US012605462B2

(12) United States Patent  
Kim et al.

(10) Patent No.: US 12,605,462 B2  
(45) Date of Patent: Apr. 21, 2026

(54) POROUS SILICON NANOPARTICLE-BASED DRUG DELIVERY SYSTEM INDUCING REACTIVE OXYGEN SPECIES AND SELF-ACTIVATION THEREOF, AND METHOD FOR PREPARING SAME

(71) Applicant: University-Industry Cooperation Group of Kyung Hee University, Yongin-si (KR)

(72) Inventors: Do Kyoung Kim, Seoul (KR); Rae Hyung Kang, Seoul (KR)

(73) Assignee: University-Industry Cooperation Group of Kyung Hee University, Yongin-si (KR)

( * ) Notice: Subject to any disclaimer, the term of this patent is extended or adjusted under 35 U.S.C. 154(b) by 46 days.

(21) Appl. No.: 17/739,616

(22) Filed: May 9, 2022

(65) Prior Publication Data

US 2023/0053600 A1    Feb. 23, 2023

(30) Foreign Application Priority Data

Aug. 2, 2021    (KR) ........................ 10-2021-0101225

(51) Int. Cl.
| | |
|---|---|
| *A61K 47/69* | (2017.01) |
| *A61K 47/52* | (2017.01) |
| *A61K 47/54* | (2017.01) |
| *A61K 47/64* | (2017.01) |
| *B82Y 5/00* | (2011.01) |

(52) U.S. Cl.
CPC .......... *A61K 47/6929* (2017.08); *A61K 47/52* (2017.08); *A61K 47/54* (2017.08); *A61K 47/64* (2017.08); *B82Y 5/00* (2013.01)

(58) Field of Classification Search
CPC .... A61K 47/6929; A61K 47/52; A61K 47/54; A61K 47/64; A61K 41/0057; A61K 47/6923; A61K 9/5146; A61K 9/5169; B82Y 5/00; A61P 35/00
See application file for complete search history.

(56) References Cited

FOREIGN PATENT DOCUMENTS

| KR | 101990214 B1 * | 6/2019 | .......... A61K 31/216 |
|---|---|---|---|
| KR | 10-2267519 B1 | 6/2021 | |

OTHER PUBLICATIONS

Gautam A, et al. Tumor homing peptides as molecular probes for cancer therapeutics, diagnostics and theranostics. Curr Med Chem. 2014;21(21):2367-91. doi: 10.2174/0929867321666140217122100. PMID: 24533809. (Year: 2014).*

Liang J, et al. ROS-responsive drug delivery systems. Bioeng Transl Med. Jul. 5, 2016;1(3):239-251. doi: 10.1002/btm2.10014. PMID: 29313015; PMCID: PMC5689534. (Year: 2016).*

Kang RH, et al. Self-Activating Therapeutic Nanoparticle: A Targeted Tumor Therapy Using Reactive Oxygen Species Self-Generation and Switch-on Drug Release. ACS Appl Mater Interfaces. Jul. 7, 2021;13(26):30359-30372. doi: 10.1021/acsami.1c07037. Epub Jun. 18, 2021. PMID: 34142813. (Year: 2021).*

Agemy L, et al. Nanoparticle-induced vascular blockade in human prostate cancer. Blood. Oct. 14, 2010;116(15):2847-56. doi: 10.1182/blood-2010-03-274258. Epub Jun. 29, 2010. PMID: 20587786; PMCID: PMC2974592. (Year: 2010).*

Chao Y, et al. Synthesis and characterisation of isothiocyanate functionalised silicon nanoparticles and their uptake in cultured colonic cells. Faraday Discuss. Jun. 19, 2020;222(0):332-349. doi: 10.1039/c9fd00087a. PMID: 32101206. (Year: 2020).*

Pocasap P, et al. Structures of isothiocyanates attributed to reactive oxygen species generation and microtubule depolymerization in HepG2 cells. Biomed Pharmacother. May 2018;101:698-709. doi: 10.1016/j.biopha.2018.02.132. Epub Mar. 22, 2018. PMID: 29522950. (Year: 2018).*

Tong F, et al. Bone-Targeting Prodrug Mesoporous Silica-Based Nanoreactor with Reactive Oxygen Species Burst for Enhanced Chemotherapy. ACS Appl Mater Interfaces. Aug. 5, 2020;12(31):34630-34642. doi: 10.1021/acsami.0c08992. Epub Jul. 21, 2020. PMID: 32635715. (Year: 2020).*

Bertucci A, et al. Tumor-Targeting, MicroRNA-Silencing Porous Silicon Nanoparticles for Ovarian Cancer Therapy. ACS Appl Mater Interfaces. Jul. 10, 2019;11(27):23926-23937. doi: 10.1021/acsami.9b07980. Epub Jun. 28, 2019. PMID: 31251556. (Year: 2019).*

Bertucci, A., et al. "Tumor-Targeting, MicroRNA-Silencing Porous Silicon Nanoparticles for Ovarian Cancer Therapy" CACS Appl. Mater. Interfaces (2019) 11, 23926-23937.

Kusaczuk, M., et al. "Silica nanoparticle-induced oxidative stress and mitochondrial damage is followed by activation of intrinsic apoptosis pathway in glioblastoma cells" International Journal of Nanomedicine (2018) 13, 2279-2294.

Wu, X., et al. "Isothiocyanates induce oxidative stress and suppress the metastasis potential of human non-small cell lung cancer cells" BMC Cancer (2010) 10:269.

Kang, R. H., et al. "Self-Activating Therapeutic Nanoparticle: A Targeted Tumor Therapy Using Reactive Oxygen Species Self-Generation and Switch-on Drug Release" ACS Appl. Mater. Interfaces (2021) 13, 26, 30359-30372.

Martínez-Edo, G. et al. "Isothiocyanate-Functionalized Mesoporous Silica Nanoparticles as Building Blocks for the Design of Nanovehicles with Optimized Drug Release Profile" Nanomaterials (2019) 9, 1219; doi: 10.3390/nano9091219.

Kang, R. H. et al. "Systematic Degradation Rate Analysis of Surface-Functionalized Porous Silicon Nanoparticles" Materials (2019) 12, 580; doi:10.3390/ma12040580.

Office Action issued for KR application No. 10-2021-0101225 dated Sep. 25, 2023, with English machine translation.

* cited by examiner

*Primary Examiner* — Maher M Haddad  
*Assistant Examiner* — Alec Jon Peters  
(74) *Attorney, Agent, or Firm* — Westman, Champlin & Koehler, P.A.; Amanda M. Prose

(57) ABSTRACT

Proposed is a porous silicon nanoparticle with isothiocyanate moiety conjugated to the surface. The porous silicon nanoparticle with isothiocyanate moiety conjugated to the surface has low side effects due to high biocompatibility, and can generate reactive oxygen species in cells without an external initiator, which can promote decomposition and release of supported drugs.

2 Claims, 18 Drawing Sheets

Specification includes a Sequence Listing.

FIG. 2

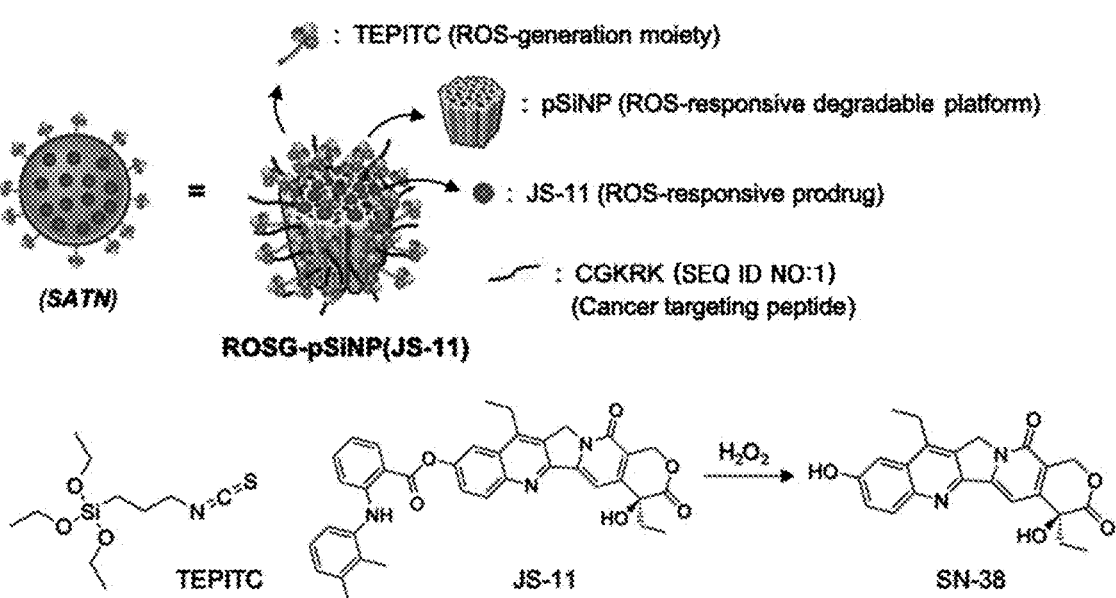

: TEPITC (ROS-generation moiety)

: pSiNP (ROS-responsive degradable platform)

: JS-11 (ROS-responsive prodrug)

: CGKRK (SEQ ID NO:1)
(Cancer targeting peptide)

(SATN)

ROSG-pSiNP(JS-11)

TEPITC     JS-11     SN-38

FIG. 3

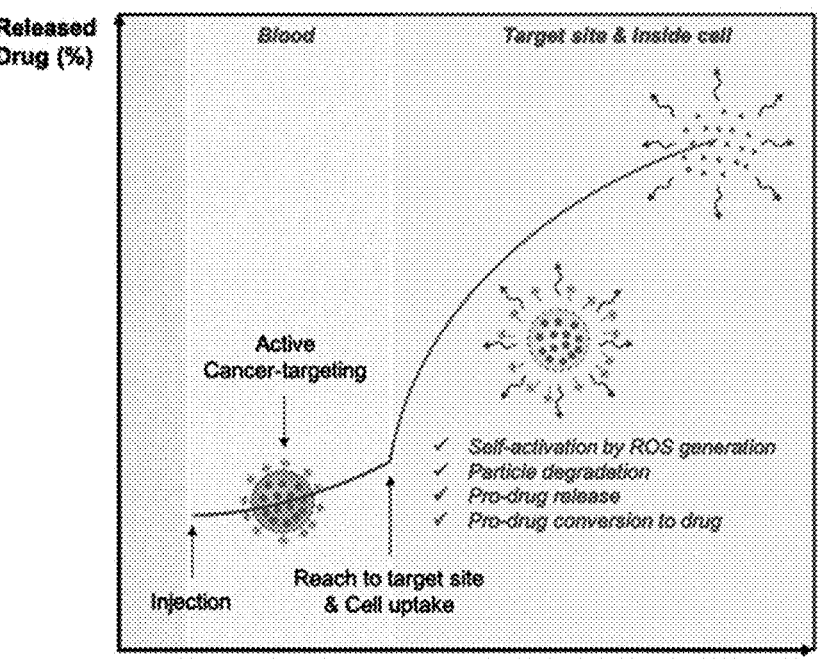

Released Drug (%)

Blood     Target site & inside cell

Active Cancer-targeting

✓ Self-activation by ROS generation
✓ Particle degradation
✓ Pro-drug release
✓ Pro-drug conversion to drug Injection Reach to target site & Cell uptake Time (DCF signal)

FIG. 7A
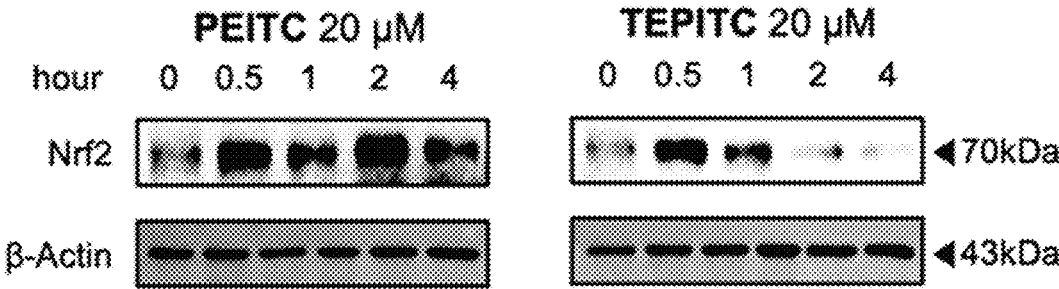
FIG. 7B
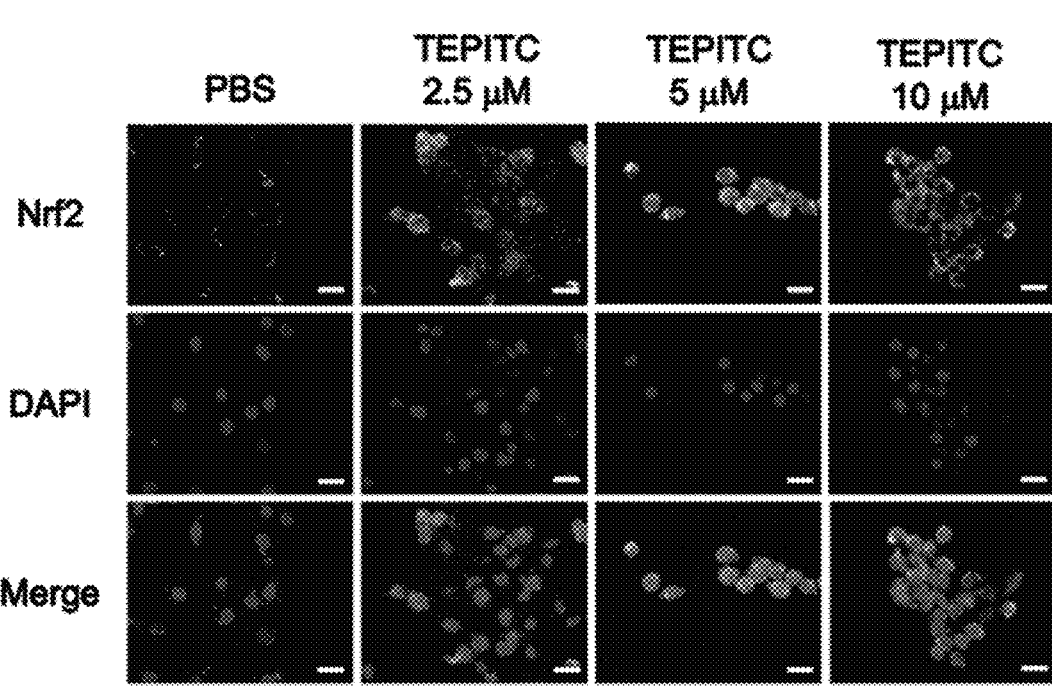
FIG. 8

FIG. 9

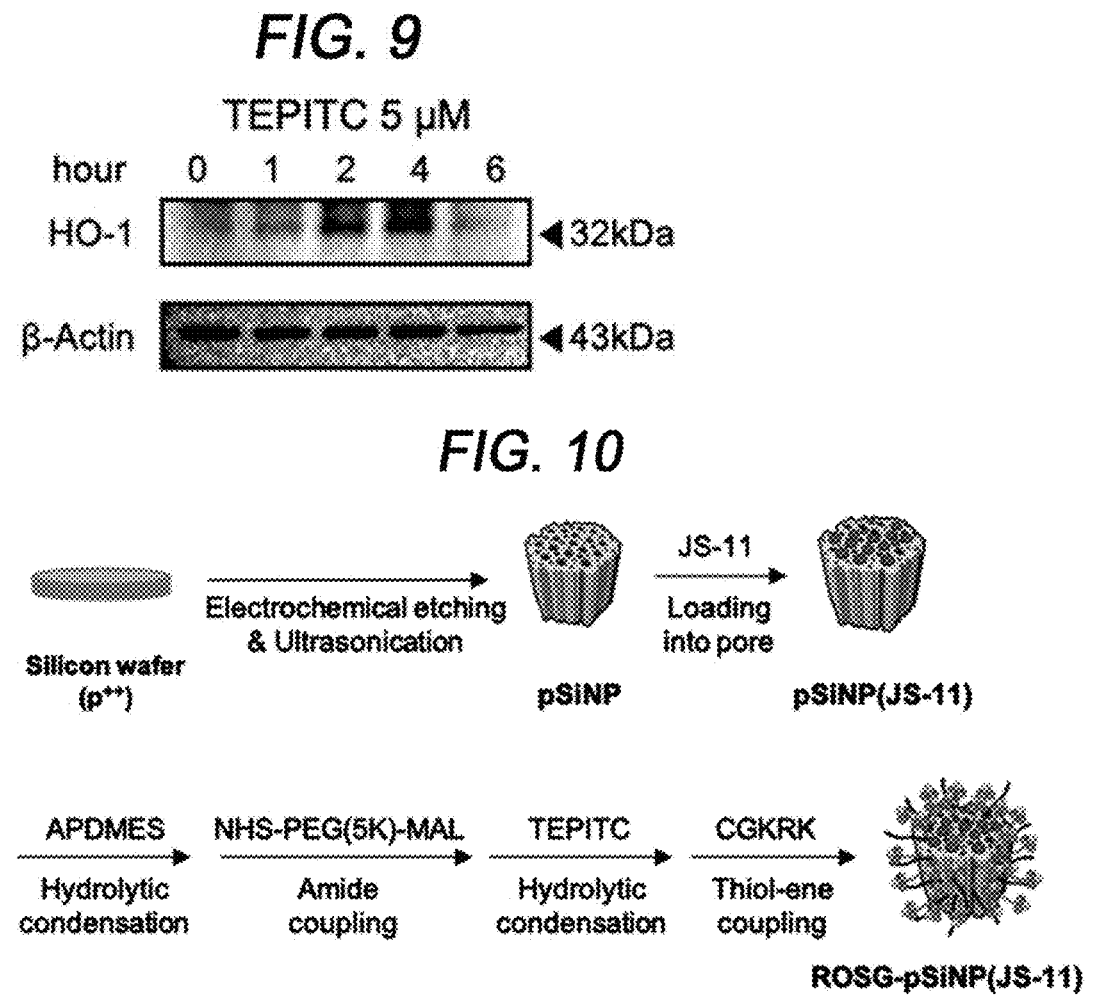

TEPITC 5 μM

| hour | 0 | 1 | 2 | 4 | 6 |
|------|---|---|---|---|---|

HO-1 ◀32kDa

β-Actin ◀43kDa

FIG. 10

Silicon wafer
(p⁺⁺) → Electrochemical etching & Ultrasonication → pSINP → JS-11 / Loading into pore → pSINP(JS-11)

APDMES / Hydrolytic condensation → NHS-PEG(5K)-MAL / Amide coupling → TEPITC / Hydrolytic condensation → CGKRK / Thiol-ene coupling →

ROSG-pSINP(JS-11)

*FIG. 12*
pSiNP                  ROSG-pSiNP(JS-11)
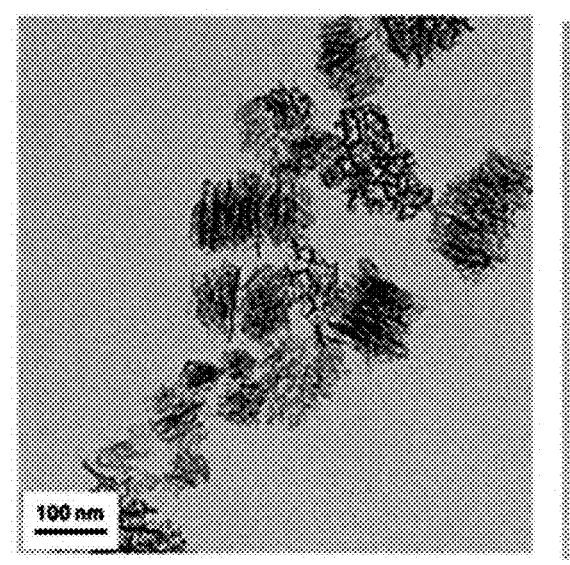 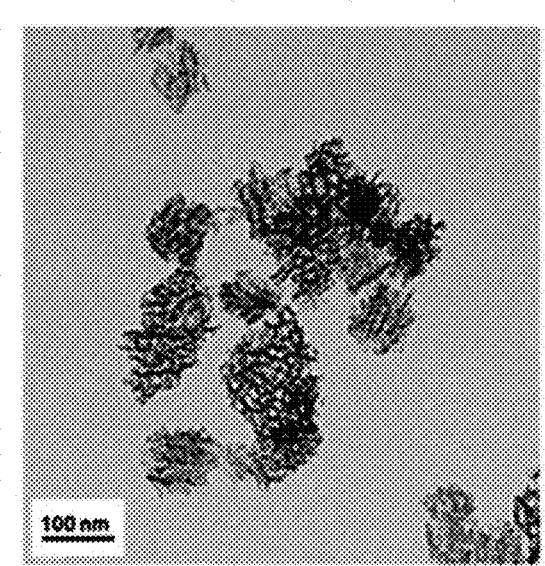
*FIG. 13*
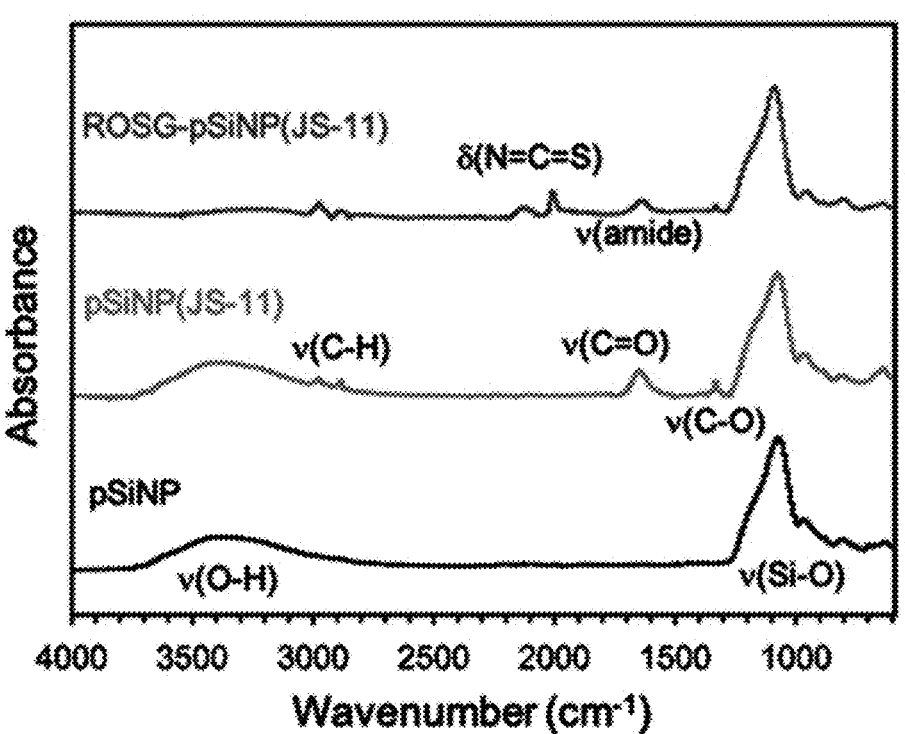

FIG. 14B
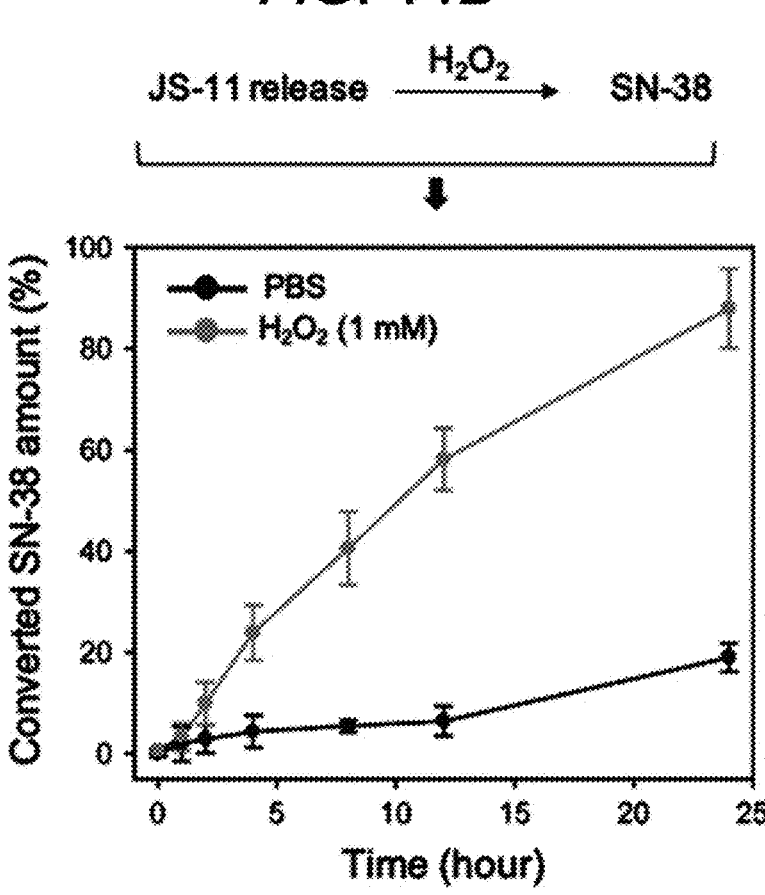
FIG. 15
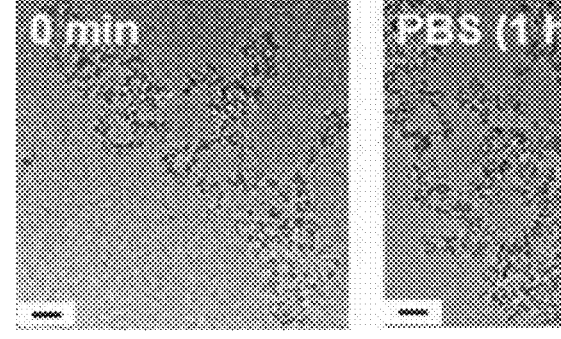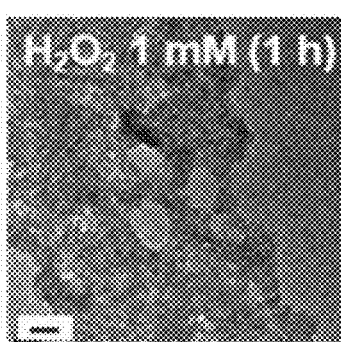

```
        a b c    a b c    a b c

Nrf2    ▬▬▬▬▬    ▬▬▬▬▬    ▬▬▬▬▬  ◀70kDa

β-Actin ▬▬▬▬▬    ▬▬▬▬▬    ▬▬▬▬▬  ◀43kDa 0.5 h      1 h      2 h
``` a: PBS
b: pSiNP
c: ROSG-pSiNP

|  | Bright field | DAPI | Fluorescein | Membrane | Merge |
| --- | --- | --- | --- | --- | --- |
| PBS |  |  |  |  |  |
| pSiNP (Fluorescein) |  |  |  |  |  |
| pSiNP-NCS (Fluorescein) |  |  |  |  |  |
| ROSG-pSiNP (Fluorescein) |  |  |  |  |  |

FIG. 20

Pancreatic cancer xenograft mice
(Cell line: BxPC-3)

Tail vein i.v.
injection

POROUS SILICON NANOPARTICLE-BASED DRUG DELIVERY SYSTEM INDUCING REACTIVE OXYGEN SPECIES AND SELF-ACTIVATION THEREOF, AND METHOD FOR PREPARING SAME

CROSS REFERENCE TO RELATED APPLICATION

The present application claims priority to Korean Patent Application No. 10-2021-0101225, filed on Aug. 2, 2021, the entire contents of which is incorporated herein for all purposes by this reference.

BACKGROUND OF THE INVENTION

1. Field of the Invention

The present disclosure relates to a porous silicon nanoparticle-based drug delivery system inducing reactive oxygen species and self-activation thereof and a method for preparing the same.

2. Description of the Related Art

Increased intracellular reactive oxygen species (ROS) in chemotherapy for tumors has been considered an intrinsic anticancer drug candidate because it can inhibit tumor growth through cell cycle inhibition and apoptosis induction.

Intracellular ROS levels can be increased through chemotherapy/radiation therapy, and the resulting ROS stress contributes to the destruction of cancer cells. To date, methods for increasing ROS as an anticancer treatment method can be broadly classified into two areas.

The first method is to induce ROS generation with an external initiator. In photodynamic therapy (PDT), ROS may be generated by administering a photosensitizer or a nano-formulation thereof and applying light as an external initiator. However, external initiators such as light have the disadvantage of being inconvenient to apply to cancer located in internal organs.

The second method is ROS generation by intracellular initiators. Metal-based nanoparticles can generate ROS by intracellular hydrogen peroxide. This reaction has the advantage of generating hydroxyl radicals by an internal initiator such as hydrogen peroxide without the need for an external initiator but has the disadvantage of having big side effects due to the inherent toxicity and non-decomposition of metal-based nanoparticles.

In addition, the existing ROS-generating nano-formulation has a limitation in that the ROS concentration is reduced due to biothiol such as glutathione and cysteine overexpressed in cancer cells.

Therefore, a nano-drug delivery system with low biotoxicity and high biodegradability that can generate ROS in cells without an external initiator can target specific cancer cells, and can deliver anticancer agents to improve the therapeutic effect is required.

DESCRIPTION OF THE RELATED ART

Patent Literatures (Patent literature 0001) Korea Patent Application Laid-open Publication No. 10-1990214 (Jun. 11, 2019)

Non-Patent Literature (Non-Patent literature 0001) ACS Appl. Mater. Interfaces 2021, 13, 26, 30359-30372 (2021 Jun. 18)

SUMMARY OF THE DISCLOSURE

According to one embodiment, provided is a porous silicon nanoparticle-based drug delivery system that induces activated oxygen species in a specific cell without an external initiator and thereby promotes self-activation and release of supported drugs.

One aspect of the present disclosure provides a drug delivery system, the drug delivery system including: porous silicon nanoparticles; and an isothiocyanate moiety conjugated to the surface of the porous silicon nanoparticle.

The porous silicon nanoparticles may support drugs and have high biocompatibility and biodegradability, thereby having low side effects. In addition, since the isothiocyanate moiety is conjugated to the surface, activated oxygen species may be generated in the cell without an external initiator, decomposition of porous silicon nanoparticles may be promoted, and the release of supported drugs may be accelerated.

The porous silicon nanoparticles may have a mesoporous structure having pores of 2 to 50 nm, a microporous structure having pores of 2 nm or less or a structure in which they are mixed.

The average diameter of the porous silicon nanoparticles may be 100 to 200 nm.

The average diameter of the drug delivery system may be 100 to 500 nm.

The isothiocyanate (ITC) is a functional group having a $-N=C=S$ structure. Referring to FIGS. 1 and 3, the drug delivery system is not activated in the blood, but when it penetrates into the cell, the isothiocyanate group and glutathione (GSH) bind together, thereby increasing the level of intracellular reactive oxygen species without an external initiator.

According to an embodiment, a drug delivery system in which an isothiocyanate-based moiety is conjugated or bonded to the surface of the porous silicon nanoparticle may be prepared by reacting the isothiocyanate-based compound with the porous silicon nanoparticles.

The isothiocyanate-based compound is not particularly limited as long as the isothiocyanate-based compound may be conjugated or bonded to the surface of the silicon nanoparticles to form an isothiocyanate-based moiety. The isothiocyanate-based compound may be, for example, triethoxy (3-isothiocyanatopropyl) silane, triethoxy (2-isothiocyanatoethyl) silane, triethoxy(4-isothiocyanatobutyl)silane, triethoxy(5-isothiocyanatopentyl)silane, diethoxy-(2-isothiocyanatoethyl)-methylsilane, diethoxy-(3-isothiocyanatopropyl)-methylsilane, diethoxy-(4-isothiocyanatobutyl)-methylsilane, 4-thiothiocyanatobutyl (trimethoxy)silane, ethoxycarbonyl isothiocyanate, and 3-isothiocyanatobenzenamine.

According to one embodiment, the isothiocyanate moiety may be directly conjugated to the surface of the porous silicon nanoparticles.

According to one embodiment, the drug delivery system may further include a drug or prodrug supported on the porous silicon nanoparticles. The drug or prodrug may be supported by 20% by weight or more based on the weight of the porous silicon nanoparticles.

The drug is not particularly limited as long as it can be supported on porous silicon nanoparticles.

The drug may be an anticancer agent. The anticancer agent, for example, may be selected from the group of a camptothecin-based anticancer agent consisting of 7-ethyl-10-hydroxycamptothecin (SN-38), paclitaxel, doxorubicin, cis-platin, docetaxel, tamoxifen, camtothecin, anasterozole, carboplatin, topotecan, belotecan, irinotecan, gleevec, monomethyl auristatin E (MMAE), mertansine (DM1), soravtansine (DM4), and vincristine.

The prodrug means that although pharmacologically active is low or inactive, the prodrug can be converted into a drug with pharmacological activity under certain conditions. The prodrug may be a derivative of a parent drug or the parent drug, and the promoiety may be conjugated through a group among an ester group, a carbonate group, a carbamate group, a urea group, an amide group, or a phosphate group. The parent drug may be the anticancer agent but is not particularly limited thereto. According to one embodiment, the prodrug may be converted into a drug exhibiting cytotoxicity in an environment within a cancer cell. The prodrug may be converted into an active drug by removing a promoiety ester-bonded with the parent drug by reactive oxygen species (ROS) or esterase. The promoiety may be at least one compound selected from the group consisting of indomethacin, aceclofenac, niflumic acid, ketoprofen, 2-(6-methoxy-2-naphthyl)propanoic acid, fenoprofen, flufenamic acid, flurbiprofen, ibuprofen, loxoprofen, mefenamic acid, and tolfenamic acid. For example, the prodrug may be JS-11 in which mefenamic acid and SN-38 are ester-bonded. The JS-11 may have the following structure.

[Structure of JS-11]

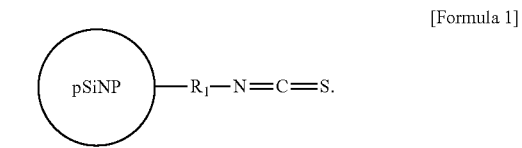

When the prodrug JS-11 is absorbed into cancer cells, mefenamic acid is removed by high ROS level or overexpressed oxygenase and converted to the anticancer drug SN-38, thereby exhibiting cytotoxicity.

According to one embodiment, the drug delivery system may further include a tumor homing peptide conjugated to the surface of the porous silicon nanoparticles. The tumor homing peptide (THP), also called a tumor targeting peptide, is a cyclic or linear peptide that specifically binds to a receptor present in a tumor. The tumor homing peptide is not particularly limited as long as the tumor homing peptide can be conjugated to the surface of the porous silicon nanoparticle or a linker and exhibits tumor specificity. More than 700 types of the tumor homing peptide are known, for example, the tumor homing peptide may be at least one peptide selected from a CGKRK-containing peptide (SEQ ID NO: 1), a CREKA-containing peptide (SEQ ID NO: 2), and an RGR-containing peptide (SEQ ID NO: 3). The tumor homing peptide may be conjugated to the surface of the porous silicon nanoparticles or to a linker attached to the surface, and the N-terminus or C-terminus of the peptide may be conjugated.

According to one embodiment, the drug delivery system may be represented by the following Formula 1:

[Formula 1]

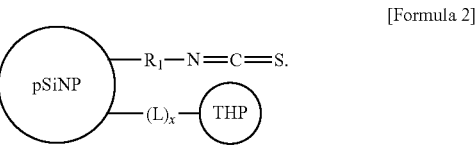

In Formula 1, pSiNP is a porous silicon nanoparticle, and $R_1$ may be an alkyl group having 1 to 8 carbon atoms. $R_1$ may be a straight-chain or branched alkyl group.

According to one embodiment, the drug delivery system may be represented by the following Formula 2:

[Formula 2]

In Formula 2, pSiNP is a porous silicon nanoparticle, $R_1$ is an alkyl group having 1 to 8 carbon atoms, the THP is a tumor homing peptide, and the L is a linker, and X is 0 or 1. $R_1$ may be an alkyl group with a straight-chain or branched chain. The THP may bind to pSiNP via or without a linker. The linker may use a linker known to those skilled in the art, for example, the linker may be one water-soluble polymer linker or two or more water-soluble polymer linkers selected from the group consisting of polyethylene glycol (PEG); polyethylene oxide (PEO); polyethyleneimine (PEI); polyvinyl alcohol (PVA); and a copolymer thereof. For example, the copolymer may include at least one water-soluble polymer selected from the group consisting of PEO-PPO-PEO, PEO-PPO-PEO, PEG-PEI, PEG-PVA, PEG-PEI-PVA, and PEI-PVA. If the linker is PEG, the molecular weight of PEG may have an average molecular weight of 500 to 20,000 Daltons, 500 to about 10,000 Daltons, 500 to 6,000 Daltons, or average molecular weight of 5,000 Daltons but is not particularly limited thereto.

In Formulae 1 or 2, $R_1$—N=C=S may be an isothiocyanate moiety. $R_1$ may be derived from an isothiocyanate-based compound. For example, when triethoxy(3-isothiocyanatopropyl)silane is subjected to a condensation reaction with pSiNP, $R_1$ may be a propyl group derived from triethoxy(3-isothiocyanatopropyl)silane.

In Formulae 1 or 2, the isothiocyanate moiety and the tumor homing peptide conjugated to the pSiNP surface are indicated one by one for convenience, but it will be apparent that a plurality of them may be conjugated.

According to one embodiment, the porous silicon nanoparticles having an isothiocyanate moiety and a CGKRK peptide (SEQ ID NO: 1) conjugated to the surface and supporting JS-11 1) specifically bind to pancreatic cancer cells and penetrate into the cells, 2) the level of reactive oxygen species is increased without an external initiator, 3) the decomposition of porous silicon nanoparticles is promoted by increasing the level of reactive oxygen species, thereby promoting the release of prodrugs, 4) converting the released prodrugs into anticancer agents, thereby killing pancreatic cancer cells specifically and efficiently.

Another aspect of the present disclosure provides a pharmaceutical composition for treating cancer, including the drug delivery system as an active ingredient.

Cancer may be, for example, prostate cancer, rectal cancer, renal cancer, ovarian cancer, endometrial cancer, thyroid cancer, pancreatic cancer, breast cancer, colon cancer, bladder cancer, brain cancer, glial cancer, melanoma cancer, pineal gland cancer, or lung cancer but is not particularly limited thereto.

The pharmaceutical composition may be administered in various oral and parenteral formulations, and when formulated, formulations may be prepared using a diluent or excipient such as a commonly used filler, extender, binder, wetting agent, disintegrant, surfactant, etc.

Formulations for oral administration include, for example, tablets, pills, hard/soft capsules, solutions, suspensions, emulsifiers, syrups, granules, elixirs, and troches. These formulations contain, in addition to the active ingredient, diluents (e.g., lactose, dextrose, sucrose, mannitol, sorbitol, cellulose and/or glycine), lubricants (e.g., silica, talc, stearic acid, and magnesium or calcium salts thereof and/or or polyethylene glycol). Tablets may contain binders such as magnesium aluminum silicate, starch paste, gelatin, methylcellulose, sodium carboxymethylcellulose, and/or polyvinylpyrrolidone, and the like, and optionally, tablets may contain a disintegrant such as starch, agar, alginic acid, or a sodium salt thereof or boiling mixture, and/or an absorbent, a colorant, a flavoring agent, and a sweetening agent.

The pharmaceutical composition may be administered parenterally, and parenteral administration may be administered by subcutaneous injection, intravenous injection, intramuscular injection, or intrathoracic injection. The pharmaceutical composition may be formulated into a formulation for parenteral administration according to a method known to those skilled in the art, for example, by mixing in water with a stabilizer or buffer to prepare a solution or suspension, which can be prepared as an ampule or vial unit dosage form. The composition may contain sterile or preservatives, stabilizers, hydrants or emulsifiers, supplements such as salts and/or buffers for controlling osmotic pressure, and other therapeutically useful substances, and it can be formulated according to a conventional method of mixing, granulating, or coating.

Another aspect of the present disclosure provides a method for preparing a drug delivery system, the method includes: preparing porous silicon nanoparticles; and conjugating an isothiocyanate moiety to the surface of the porous silicon nanoparticle.

The detailed description of the porous silicon nanoparticles and the isothiocyanate moiety is the same as described above.

Porous silicon nanoparticles may be prepared by methods known to those skilled in the art. For example, the porous silicon nanoparticles may be prepared by electrochemically etching and ultrasonic fragmenting a boron-doped p⁺⁺-type silicon wafer but are not limited thereto.

According to one embodiment, conjugating the isothiocyanate moiety to the surface of the porous silicon nanoparticles may be performed by reacting the isothiocyanate-based compound on the surface of the porous silicon nanoparticles. For example, the isothiocyanate-based compound may be directly conjugated to Si of the porous silicon nanoparticles by a condensation reaction, and for an example of a structure to which they are conjugated, refer to Formula 3 of the Example. Examples of the isothiocyanate-based compound are the same as described above.

The preparing method may further include supporting a drug or prodrug on the porous silicon nanoparticles. The supporting may be performed, for example, by mixing a drug or a prodrug with porous silicon nanoparticles and vortex mixing. The supporting of the drug or prodrug may be performed before the isothiocyanate moiety is conjugated to the surface of the porous silicon nanoparticle. The description of the drug or prodrug is the same as described above.

The preparation method may further include conjugating the tumor homing peptide to the surface of the porous silicon nanoparticles. The conjugation may be in which the tumor homing peptide binds to the surface of the porous silicon nanoparticle or to a linker conjugated to the surface. The conjugating of the tumor homing peptide may be performed before or after the isothiocyanate moiety is conjugated to the surface of the porous silicon nanoparticle.

Another aspect of the present disclosure provides a method of treating cancer, the method includes administering the drug delivery system to an individual in a pharmaceutically effective amount.

The "pharmaceutically effective amount" means an amount sufficient to treat or prevent disease with a reasonable benefit/risk ratio applicable to medical treatment or prevention, and the effective dose level can be determined according to the severity of the disease, the activity of the drug, and the age, body weight, health, sex of the patient, patient's sensitivity to drug, administration time, administration route and excretion rate, duration of treatment, factors including drugs used in combination with or concurrently with the composition of the present disclosure used, and other factors well known in the medical field.

The administration may be intraperitoneal administration, intravenous administration, intramuscular administration, subcutaneous administration, endothelial administration, oral administration, topical administration, intranasal administration, intrapulmonary administration, and intraarterial administration, or rectal administration, but is not particularly limited thereto.

The drug delivery system, according to one embodiment, induces intracellular reactive oxygen species without an external initiator, and thereby self-activating and promoting the release of supported drugs.

The drug delivery system, according to one embodiment, is specific to a cancer cell and induces reactive oxygen species without an external initiator, thereby promoting cancer cell-specific release of the supported drug or prodrug, thereby providing excellent anticancer effect and reducing side effects.

The drug delivery system, according to an embodiment, exhibits excellent therapeutic effects in cell and animal experiments and has excellent biocompatibility and selective drug release for cancer cells, so it has the advantage of lower side effects than existing anticancer drugs and ROS-generating nano-formulations.

BRIEF DESCRIPTION OF THE DRAWINGS

FIG. 2 shows a drug delivery system prepared with TEPITC, pSiNP, JS-11, and CGKRK peptides (SEQ ID NO: 1);

FIG. 3 shows a process in which a drug delivery system, according to an embodiment, is activated in tumor cells without being activated in the blood to release the drug and shows a synergistic effect leading to an increase in ROS, the release of a prodrug, and activation of a prodrug in the tumor cells;

FIG. 7 shows the results of confirming the effect of TEPITC on Nrf2 expression in BxPC-3 cells by Western blot;

FIG. 8 shows the results of confirming the effect of TEPITC on Nrf2 expression in BxPC-3 cells by immuno-fluorescence;

FIG. 9 shows the results of confirming the effect of TEPITC on HO-1 expression in BxPC-3 cells by Western blot;

FIG. 10 shows a process for preparing a porous silicon nanoparticle drug delivery system, including an isothiocya-nate moiety, a tumor homing peptide, and a prodrug;

FIG. 12 shows a transmission electron microscope (TEM) image of pSiNP and ROSG-pSiNP (JS-11);

FIG. 13 shows the ATR-FTIR spectral analysis results of pSiNP, pSiNP (JS-11), and ROSG-pSiNP (JS-11);

FIG. 15 is a result of confirming the decomposition and shape change of ROSG-pSiNP according to the environment of hydrogen peroxide by TEM;

FIG. 20 shows the results of confirming the cytotoxicity of pSiNP, JS-11, pSiNPs (JS-11), and ROSGpSiNP (JS-11) to the BxPC-3 cell lines;

DESCRIPTION OF THE PREFERRED EMBODIMENTS

Figure 1:
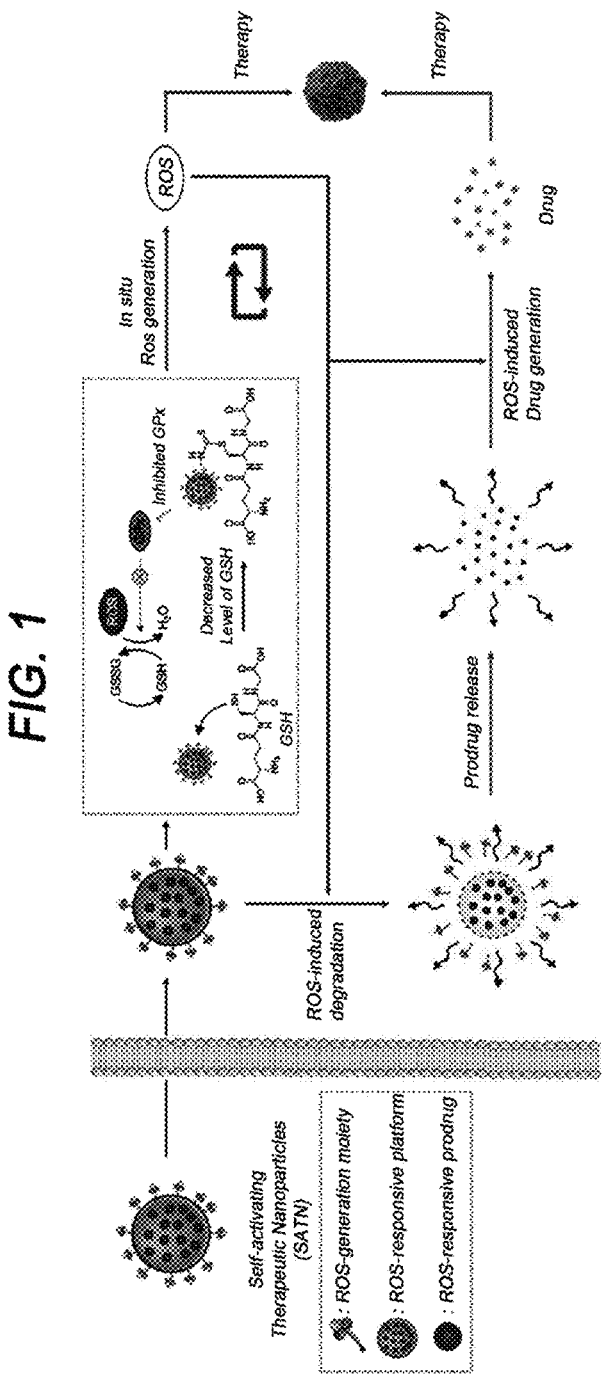
FIG. 1 shows a process in which a drug delivery system, according to an embodiment, is self-activated in a cell.

Hereinafter, one or more specific embodiments will be described in more detail through examples. However, these examples are for illustrative purposes of one or more embodiments, and the scope of the present disclosure is not limited to these examples.

Experimental Method 1-1. Cell Culture

BxPC-3, AsPC-1, and PANC-1 cell lines were obtained from the American Type Culture Collection (ATCC, Manas-sas, VA, U.S.A.). Cells were cultured in RPMI-1640 supple-mented with 10%0 (v/v) fetal bovine serum (FBS), 100 U/mL penicillin and streptomycin at 5% $CO_2$, 37° C. con-ditions.

1-2. Analysis of PEITC/TEPITC-Induced Intracellular ROS Generation

The intracellular ROS levels of cells were analyzed using the 2',7'-dichlorofluorosine diacetate (DCFDA/$H_2$DCFDA) cell ROS detection analysis kit. BxPC-3, AsPC-1, and PANC-1 cells ($1\times10^5$ cells/mL, 100 µl/well) were inoculated into 96-well black plates and incubated at 37° C. for 24 hours. The cells were then treated with PEITC or TEPITC at 1.25, 2.5, 5, 10, and 20 µM, respectively, and then incubated at 37° C. for 2 hours. As a positive control group, a set treated with hydrogen peroxide ($H_2O_2$) was prepared. The cells were then treated with 20 µM DCFDA (100 µl) at 37° C. for 45 minutes. Excitation/emission wavelengths at 485/535 nm were measured with a microplate reader (Fluorostar Omega, BMG Labtech, Germany). Intracellular ROS gen-eration was assessed by CLSM (LSM800, Carl Zeiss, Oberkochen, Germany) imaging using BxPC-3 cells. BxPC-3 cells ($1\times10^5$ cells/mL, 2 mL) were inoculated into confocal plates. After 24 hours incubation, cells were treated with 20 µM PEITC and TEPITC for 2 hours. The cells were then stained with 20 µM DCFDA (200 µL) at 37° C. for 45 minutes, washed 3 times with PBS, and stained with DAPI for 10 minutes. After washing 3 times, the cells were fixed with 4% paraformaldehyde for 20 minutes. The excitation and emission channels are: DAPI (405 nm, 400-520 nm band filter), ROS (488 nm, 400-585 nm band filter).

1-3. Porous Silicon Nanoparticles Preparation

An electrolyte solution in which 48% aqueous hydroflu-oric acid (HF) and absolute ethanol were mixed in a volume ratio of 3:1 on a p$^{++}$-type single crystal silicon wafer doped with boron at a high concentration was treated and electro-chemically etched to generate a porous sacrificial layer. Then, the porous sacrificial layer was removed using 2 M potassium hydroxide solution (KOH).

Then, a perforated etching waveform was applied to form a porous silicon layer. 300 cycles of low current density pulses of 46 mA cm$^{-2}$ for 1.8 seconds and high current density pulses of 334 mA cm$^{-2}$ for 0.4 seconds were repeated. Then, the porous silicon layer was lifted off from the silicon wafer by applying a current density of 3 mA cm$^{-2}$ in a solution composed of 7.5% aqueous HF in ethanol for 300 seconds to obtain a pSi film.

The pSi film was placed in a sealed glass vial (22.18 mL size, VWR, Catalog No. 66011-143, Radnor, PA, USA) containing deionized water (DI H$_2$O, 6 mL) in an ultrasonic bath (VWR, model number VWRA142-0307, Radnor, PA, USA) for 24 hours to obtain porous silicon nanoparticles (pSiNPs).

Porous silicon nanoparticles (pSiNPs) were incubated in DI H$_2$O (12 mL) at 25° C. for 10 days to form a silicon oxide layer on the surface of the porous silicon nanoparticles, followed by filtering with a 0.22 μm syringe filter (Millipore, Millex syringe filter unit, 220 nm model number SLGP033RS, Burlington, MA, USA). The filtered pSiNPs were then collected by centrifugation (14,000 rpm, 30 minutes) and redispersed/washed with EtOH (3 times).

1-4. Preparation of pSiNP (JS-11)

pSiNP (to 1 mg) and JS-11 stock solution (20 mg/mL DMSO, 50 μL) were dispersed in EtOH (1.45 mL) and was mixed at 25° C. for 24 hours with a vortex mixer (600 rpm, Scientific Industries, Inc., Vortex-Genie 2, model No. SI-0246, Bohemia, NY, USA). The pSiNP loaded with JS-11 was centrifuged (14,000 rpm, 15 minutes) and washed with EtOH (3 times) to remove unloaded free JS-11.

To analyze the JS-11 loading efficiency, the supernatant from each centrifugation step was analyzed by measuring UV/vis absorption spectra using a spectrophotometer (Agilent Technologies Cary 8454, U.S.A.).

pSiNP supported with JS-11 (pSiNP (JS-11), 1 mg/100 μl DI H$_2$O) was mixed with a 2 μM CaCl$_2$) stock solution (900 μl) for 90 minutes to prevent the release of JS-11 during the surface modification step. pSiNP (JS-11) was purified by centrifugation (14,000 rpm, 15 min) using DI H$_2$O, 30% EtOH, 70% EtOH, and 100% EtOH.

1.5 Preparation of ROSG-pSiNP (JS-11)

pSiNP (JS-11) (to 1 mg) and 3-aminopropyldimethylethoxysilane (APDMES, 20 μl) were mixed in EtOH (1 mL) and was vortex-mixed at 25° C. for 4 hours using vortex mixer (600 rpm, Scientific Industries, Inc., Vortex-Genie 2, Model No. SI-0246, Bohemia, NY, U.S.A.).

Amine-terminated nanoparticles were separated by centrifugation (14,000 rpm, 15 minutes), washed with EtOH (3 times), and then mixed 100 μl of maleimide-PEG-N-hydroxysuccinimide (MAL-PEG-NHS, MW=5 kDa)(10 mg/mL in EtOH) and reacted at 25° C. for 2 hours. The resulting particles were centrifuged (14,000 rpm, 15 minutes) and washed with EtOH (3 times) to remove unreacted MAL-PEG-NHS. The resulting particles were resuspended in EtOH (1 mL), and 3-isothiocyanatopropyltriethoxysilane (TEPITC, 20 μl) was added. The mixture was vortex-mixed at 25° C. for 4 hours using vortex mixer (600 rpm, Scientific Industries, Inc., Vortex-Genie 2, model number SI-0246, Bohemia, NY, USA), then centrifuged (14 000 rpm, 15 minutes) and washed with EtOH 3 times.

For targeting peptide conjugation, nanoparticle-containing EtOH (100 μL) was added to a CGKRK peptide (SEQ ID NO: 1) stock solution (1 mg/mL in DI H$_2$O, 100 μL) and incubated at 4° C. for 4 hours. Finally, the resulting nanoparticles were purified by centrifugation with EtOH (3 times) and dispersed in DI H$_2$O (10 μl, stored at 4° C. before use).

1-6. Nanoparticle Characterization

The fluid-dynamic size and zeta potential of pSiNP, pSiNP (JS-11), and ROSG-pSiNP (JS-11) were analyzed with a Malvern Instruments Zetasizer Nano ZS90 (Worcestershire, UK). The shape of nanoparticles was observed with a transmission electron microscope (TEM, Tecnai, G2 F30ST, FEI Company, OR, U.S.A.) at the Korea Basic Science Center (Korea University, Seoul, Korea). Attenuated total reflection Fourier transform infrared spectroscopy (FT-IR spectroscopy) results were obtained with a Thermo Scientific Nicolet iS 5 FT-IR spectrometer instrument (64 scans, Waltham, MA, U.S.A.).

1-7. CLSM Analysis for Cellular Uptake

The intracellular distribution of nanoparticles and intracellular ROS analysis were evaluated using BxPC-3 cells and confocal laser scanning microscopy (CLSM). Cells were inoculated in confocal dishes containing 2 mL of RPMI-1640 supplemented with 10% FBS and 1% penicillin/streptomycin at a density of 1×10$^5$ cells/mL. After incubation at 37° C. for 24 hours, the medium was replaced with RPMI-1640 containing 100 g/mL fluorescein-loaded pSiNP, fluorescein-loaded pSiNP containing TEPITC functionalization, and fluorescein-loaded pSiNP containing TEPITC/CGKRK (SEQ ID NO: 1) functionalization. After 24 hours, the cells were washed 3 times with PBS (pH 7.4), and dyes (DAPI and cell mask plasma membrane) were used for nuclear and membrane staining. After washing 3 times with PBS (pH 7.4), the cells were fixed with 4% paraformaldehyde and incubated for 20 minutes. The excitation and emission channels are: DAPI (405 nm, 400-520 nm band filter), fluorescein (488 nm, 400-585 nm band filter) and cell membrane (640/670±20 nm).

1-8. Analysis of Intracellular ROS Generation Induced by Nanoparticles

Nanoparticle-induced intracellular ROS was measured using the DCFDA/H2DCFDA Cell ROS Detection Assay Kit according to the manufacturer's protocol. BxPC-3 cells (1×10$^5$ cells per well) were inoculated in 96-well black plates and incubated at 37° C. for 24 hours. The cells were then treated with 6.25, 12.5, 25, 50, and 100 μg/mL of pSiNP, JS-11, pSiNP (JS-11), and ROSG-pSiNP (JS-11) and incubated for 5 hours (the amount of JS-11 was calculated using the loading efficiency of pSiNP (JS-11)). After incubation, 20 μM DCFDA reagent (100 μl) was added to each well, followed by incubation at 37° C. for 45 minutes.

Fluorescence excitation/emission wavelengths (485/535 nm) were measured using a microplate reader (FLUOstar Omega, BMG LABTECH, Germany). Nanoparticle-induced intracellular ROS generation was monitored by CLSM imaging of BxPC-3 cells.

Cells (1×10$^5$ cells/mL, 2 mL) were inoculated in confocal dishes. After incubation for 24 hours, cells were treated with 100 g/mL pSiNP and ROSG-pSiNP (except JS-11) at 37° C. for 2 hours and then stained with 20 μM DCFDA (200 μL) at 37° C. for 45 minutes. Cells were washed 3 times with PBS and then stained with DAPI for 10 minutes. After washing 3 times, the cells were fixed with 4% paraformaldehyde for 20 minutes. Finally, intracellular ROS was observed. The excitation and emission channels were DAPI (405 nm, 400-520 nm band filter) and ROS (488 nm, 400-585 nm band filter), respectively.

1-9. Laboratory Animal Preparation

BALB/c nude mice (females and males, 4 weeks and 5 weeks old) were commercially obtained from Nara Co., Ltd., Gyeonggi-do, Korea. BxPC-3 cells (5×10$^6$ cells, suspended in 100 μl mixture of RPMI medium and Matrigel, 1:1) were injected subcutaneously behind the flank of each mouse. All animal experiments were performed according to the guidelines of the Korea Kyunghee University Animal Care Committee (IACUC).

1-10. Biodistribution Analysis

IVIS imaging was performed to confirm the biodistribution of nanoparticles in xenograft mice. Mice with xenograft tumors were randomly assigned to 4 groups (females, n=3 per group). IVIS imaging experiments were performed when the longest diameter of the subcutaneous tumor reached to 10 mm. Mice in each group were divided into the following four groups. (1) control group (PBS intravenous injection (i.v.)), (2) pSiNP group (pSiNP intravenous injection), (3) pSiNP(JS-11) group (pSiNP(JS-11) intravenous injection), and (4) ROSG-pSiNP group (JS-11) (ROSG-pSiNP (JS-11) intravenous injection). Particles (20 mg/kg in 100 μl PBS suspension) were injected intravenously (i.v.) into mice and mice were sacrificed 2 hours later. The fluorescence signals of the resected tumor/major organs (lung, heart, liver, spleen, kidney) were measured using the VISQUE In Vivo Smart LF luminescence and fluorescence animal imaging system (Vieworks Co., Ltd., Korea), and GFP excitation ($\lambda_{ex}$=390 to 490 nm) and an ICG emission filter ($\lambda_{em}$=810 to 860 nm) were used.

1-11. Therapeutic Efficacy Assay

Tumor-bearing mice were randomly divided into 5 groups (n=5 per group). (1) PBS only, (2) pSiNP only, (3) JS-11, (4) pSiNP (JS-11), and (5) ROSG-pSiNP (JS-11) were administered by intravenous injection (i.v.) 4 times at intervals of 3 days at a dose of 20 mg/kg, 100 μl each.

The mouse tumor size was recorded every 3 days until the end of the experiment, and the tumor volume was calculated by the formula V=[(tumor length)×(tumor width)$^2$]/2.44. At the end of the experiment (day 22), the body of each mouse was photographed with a digital camera, and body weight was measured.

The experiment was terminated considering the conditions of the control group according to the Guidelines for Endpoint Monitoring and Humane Termination of the IACUC. Tumors of each mouse were collected after whole blood perfusion using ethylenediaminetetraacetic acid (EDTA) coated tubes after anesthesia.

Tumor growth inhibition T/C ratio (ratio of mean tumor weight of treatment group to control group) was used to calculate treatment efficacy. The tumor growth inhibition T/C ratio equation is as follows. T/C ratio=$(T_t/T_0)/(C_t/C_0)$, where $T_t$=median tumor volume treated at time t, $T_0$=median tumor volume treated at time 0, $C_t$=median tumor in control group at time t volume, and $C_0$=median tumor volume of the control group at time 0).

For histological analysis, dissected organs (liver, kidney, spleen, heart, and lung) and tumors were immersed in 10% formalin solution. After blood coagulation, serum was separated by centrifugation at 4,000×g for 30 minutes immediately for hematological analysis. All experiments using animals were performed according to the guidelines and protocols approved by IACUC, Kyunghee University, Seoul, Korea.

<Example 1> Nanoparticle Design for Self-Activation Therapy

Based on ROS generation by ITC, ROSG-pSiNP-(JS-11), a self-activating therapeutic nanoparticles (SATN) system consisting of the following four main components was prepared. (See FIG. 2)

(i) 3-isothiocyanatopropyltriethoxysilane (TEPITC): it is a ROS generating moiety. The TEPITC moiety can be functionalized on the surface of pSiNPs via a condensation reaction in an ethanol solvent. Specifically, the pSiNP surface can be functionalized through the condensation reaction of triethoxysilane ($(C_2H_5O)_3Si$) of the TEPITC moiety and silanol (Si—OH) of the pSiNP surface in an ethanol solvent. According to one embodiment, the surface-functionalized pSiNP may be represented by Formula 3 below:

[Formula 3]

(ii) pSiNP (porous Si Nanoparticle): it is a drug delivery platform that is degraded in response to ROS. pSiNP can be decomposed in a physiological environment and can accelerate decomposition when exposed to ROS.

(iii) JS-11: it is a ROS-reactive prodrug conjugated with mefenamic acid and SN-38. The mefenamic acid ester moiety of JS-11 can be cleaved by ROS to release the anticancer drug SN-38. Double-shielded formulations by prodrug formulation and nanoparticle encapsulation can increase the therapeutic effect of SN-38 and reduce side effects.

(iv) CGKRK: it is a cancer-targeting peptide. (SEQ ID NO: 1). CGKRK has a high binding affinity for neovascular endothelial cells, so it can strengthen the intravascular penetration of nanoparticles and also enhance cell penetration of nanoparticles.

The nanoparticles combined with (i) to (iv) were expected to cause an ensemble action of cancer-targeting, in situ ROS self-generation for ROS-mediated treatment, and ROS-mediated self-activation (decomposition of nanoparticles, release of prodrugs, and conversion to drugs of released prodrugs) (refer to FIG. 3). A drug delivery system capable of self-activation and turn on-type drug release within a target can solve the problems of drug release due to non-specific degradation and non-cancer targeting of the existing DDS platform.

<Example 2> Intracellular ROS Upregulation and Cytotoxicity of the Isothiocyanate Moiety 2-1. Upregulation of Intracellular ROS of Isothiocyanates Cells were contacted with ITC, and intracellular ROS generation was assessed. Human pancreatic cell lines BxPC-3, AsPC-1, and PANC-1 were treated with TEPITC, and ROS levels were measured using the DCFDA/DCF kit. When 2',7'-dichlorofluorescein diacetate (DCFDA) diffuses into cells, it is deacetylated to $H_2DCF$ by cellular esterase, and when $H_2DCF$ comes into contact with ROS, it is converted to green fluorescent DCF. Phenethyl isothiocyanate (PEITC) and $H_2O_2$ were used as positive control groups. Each chemical substance (TEPITC, PEITC, and $H_2O_2$, concentration=0 to 20 μM) were treated on the cell line and incubated for 2 hours.

Figure 4:
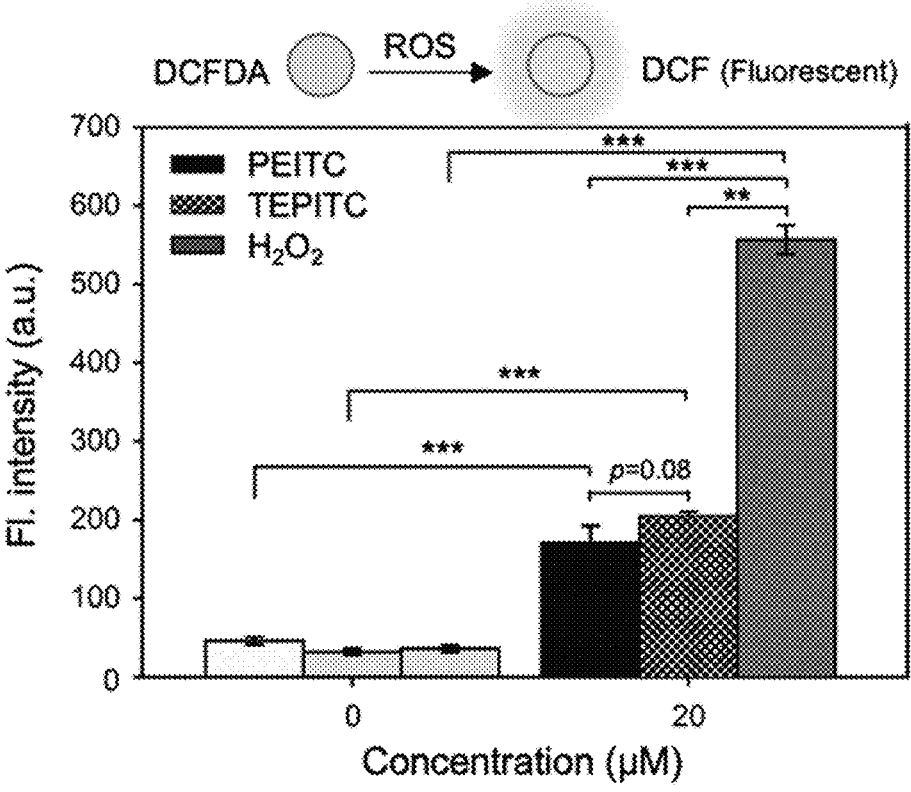
FIG. 4 shows the results of confirming the effect of TEPITC on the ROS level in pancreatic cancer cells (BxPC-3) by DCF fluorescence.

According to FIG. 4, cells treated with TEPITC showed a significant increase in fluorescence within the cytoplasm, indicating that the in situ ROS level was upregulated. Compared with before chemical treatment, the fluorescence intensity-based enhancement factor was 6.34 times higher in the TEPITC (20 μM) treatment group and 3.67 times higher in the PEITC (20 μM) treatment group.

Figure 5:
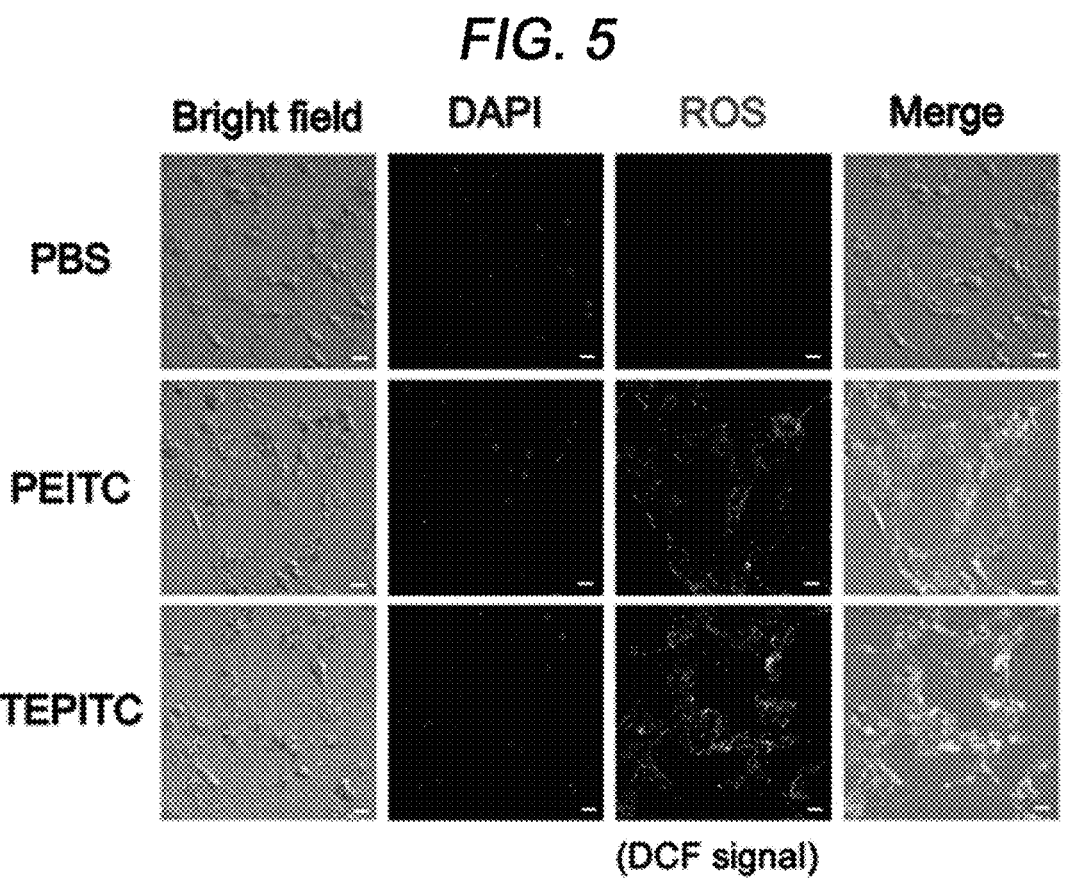
FIG. 5 shows the results of confirming the effect of TEPITC on the ROS level in pancreatic cancer cells (BxPC-3) with a CLSM image.

According to fluorescence analysis and confocal laser scanning microscopy (CLSM) images, TEPITC upregulates the intracellular ROS level, and the effect was superior to PEITC, which is known for its anticancer effect. (See FIG. 5).

2-2. Cytotoxicity of Isothiocyanates

Figure 6:
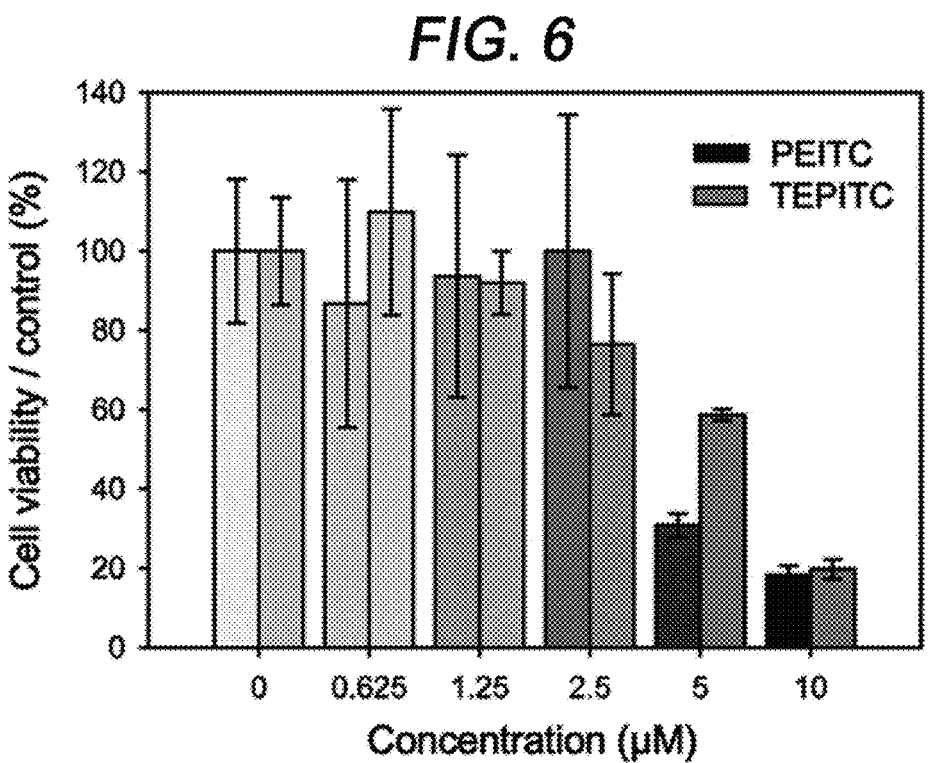
FIG. 6 is a result confirming the cytotoxicity of TEPITC.

Next, the cytotoxicity of TEPITC was analyzed. BxPC-3 cells were treated with 0 to 10 μM of TEPITC or PEITC and incubated for 24 hours, and cytotoxicity and viability were analyzed by CCK-8 assay. According to FIG. 6, both TEPITC and PEITC showed similar cytotoxicity results in a dose-dependent manner, and the cytotoxicity of BxPC-3 cells treated with 10 μM TEPITC was significantly increased up to 80% compared to the untreated group cells. Similar results were observed in other cell lines including AsPC-1 and PANC-1.

2-3. Relationship of Isothiocyanates with Nrf2/HO-1 Oxidative Stress Signaling

Oxidative stress-related signaling pathways were analyzed to confirm the association between TEPITC treatment and intracellular ROS upregulation. PEITC was used as a positive control group. PEITC is known to induce Nrf2 accumulation in human prostate cancer PC-3 cells and increase the expression of endogenous heme oxygenase-1 (HO-1) protein.

According to FIG. 7A, BxPC-3 cells were treated with TEPITC 20 μM or PEITC 20 μM and incubated for 0 to 4 hours, as a result of incubation, the expression of a regulator of cell resistance to oxidative stress, nuclear factor erythroid 2-related factor 2 (Nrf2), was significantly increased. Both the TEPITC-treated group and the PEITC-treated group showed the greatest increase in Nrf2 expression when 30 minutes had elapsed after incubation. It is noteworthy that the expression of Nrf2 in the TEPITC treatment group was maximum 30 minutes after incubation began but decreased from 1 hour later. This indicates that the stimulation of TEPITC on the oxidative stress signaling pathway of cells may be subject to time constraints. According to FIG. 7B, as a result of treatment with TEPITC at a concentration of 0 to 20 μM an increase in Nrf2 level by TEPITC was observed to be concentration-dependent in the range of 2.5 to 10 μM.

CLSM imaging was used to verify that TEPITC induces nuclear translocation of cytoplasmic Nrf2. BxPC-3 cells were treated with TEPITC (0 to 10 μM), incubated for 30 minutes, and visualized by treatment with Nrf2 antibody and DAPI.

According to FIG. 8, the immunofluorescence results were consistent with the Western blot results. An increase in Nrf2 expression in the cytoplasm was observed in the TEPITC (2.5 μM) treatment group, and in the nucleus Nrf2 expression was observed in the TEPITC (5 μM) treatment group at a concentration twice as high. The Nrf2 signal in the nucleus was weakened in the TEPITC (10 μM) treatment group at a concentration four times higher than this, and the Nrf2 signal appeared mainly in the cytoplasm.

The expression level of HO-1, an antioxidant enzyme essential for cell protection against oxidative stress, was also analyzed. Cells were treated with TEPITC (5 μM) and incubated for 0 to 6 hours. According to FIG. 9, the expression level of intracellular HO-1 was significantly increased by TEPITC. This is thought to be because Nrf2 is a transcription factor that regulates the expression of HO-1. The level of Nrf2 was maximum at 0.5 to 1 hour points, whereas the expression amount of HO-1 was the highest at 2 hours and 4 hours, but decreased from 6 hours.

In summary, isothiocyanate may affect the Nrf2/HO-1 signaling system by increasing the intracellular ROS level and may have a cancer cell killing effect by exhibiting cytotoxicity.

<Example 3> Preparation and Characterization of ROSG-pSiNP (JS-11)

Based on the results of intracellular ROS generation by TEPITC, a SATN formulation was prepared in which TEPITC was functionalized on the surface of pSiNP and containing the ROS-responsive prodrug JS-11 in the pores of pSiNP A preparing process will be described with reference to FIG. 10. A porous silicon film was prepared by electrochemically etching a p++-type silicon wafer doped with boron at a high concentration, and pSiNPs were prepared by ultrasonic fragmentation. The prodrug JS-11 was mixed with pSiNPs together with calcium ions (Ca$^{2+}$) and vortex-mixed to load JS-11 into the pores of pSiNP (3-aminopropyl)-dimethylethoxysilane (APDMES) was treated on pSiNP (JS-11) to modify the surface of pSiNP to generate a primary amine group. A polyethylene glycol (PEG) linker, maleimide-PEG-N-hydroxysuccinimide (MAL-PEG-NHS) (5 kDa), was conjugated to the primary amine on the surface of pSiNP (JS-11) through amide coupling. Next, TEPITC was grafted onto the nanoparticle surface through hydrolytic condensation. Finally, the CGKRK tumor-targeting peptide (SEQ ID NO: 1) was conjugated by a thiolene coupling reaction between the maleimide terminus of PEG and the cysteine terminus of the peptide. The prepared nanoparticles were named ROSG-pSiNP (JS-11).

When ROSG-pSiNP (JS-11) is administered, ROSG-pSiNP (JS-11) may be accumulated in the tumor site due to the homing property of CGKRK (SEQ ID NO: 1), and penetrates into the cancer cell to generate in situ ROS. By inducing degradation of pSiNP by ROS, a prodrug supported thereon is released, and finally, since the prodrug can be converted into a drug by ROS, a cancer cell-specific and high therapeutic effect and reduced side effects can be expected.

JS-11 was synthesized by a carbodiimide coupling reaction between mefenamic acid and 7-ethyl-10-hydroxycamptothecin (SN-38). (yield 95.5%). Mefenamic acid is a class of nonsteroidal anti-inflammatory drugs (NSAIDs) used to treat pain. JS-11 where mefenamic acid and SN-38 are ester-bonded can be cut by H$_2$O$_2$ treatment and converted to SN-38, and hence can be used as a prodrug reacting to ROS. The purity of JS-11 was confirmed by $^1$H/$^{13}$C nuclear magnetic resonance (NMR) and high-resolution mass spectrometry (HR-MS).

To confirm whether JS-11 is converted to SN-38 by ROS, the change in the emission spike of JS-11 using H$_2$O$_2$ at 37° C. was measured. Since JS-11 has no electron push-pull capability, there is no emission in aqueous media but decomposes upon exposure to H$_2$O$_2$ and fluoresces at 560 nm. JS-11 reacted only with H$_2$O$_2$ and did not show the conversion to SN-38 under various pH conditions (pH 3 to 10), metal ions, and biomolecules.

Figures 11A, 11B:
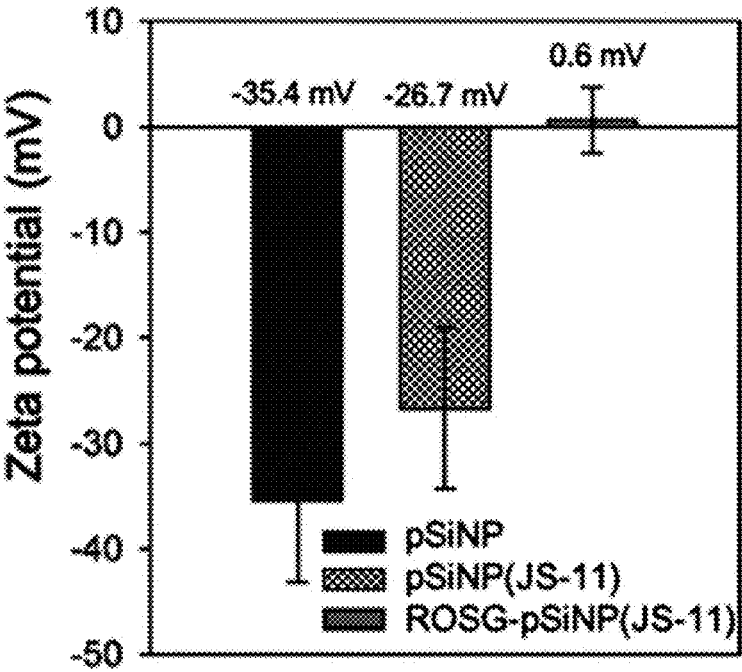
FIG. 11 shows the diameter and zeta potential of pSiNP, pSiNP (JS-11), and ROSG-pSiNP (JS-11)

The diameter and zeta potential of the pSiNP nanoparticles were measured. According to FIG. 11, it was seen that the average fluid-dynamic diameter of pSiNPs was uniform (172.2±56.7 nm, polydispersity index (PDI)=0.105). As a result of measuring the zeta potential by dynamic light scattering (DLS), it showed a negative zeta potential value of −35.4±7.75 mV JS-11-loaded nanoparticles, pSiNPs (JS-11), slightly increased in size (194.3±86.7 nm, PDI=0.229)

and slightly decreased in negative surface charge (−26.7±7.66 mV). The APDMES-modified pSiNP (JS-11) had a significant change in zeta potential (25.9±9.22 mV) due to the positive primary amine functional group of APDMES. MAL-PEG-NHS-conjugated pSiNPs (JS-11) showed a slightly reduced zeta potential (13.7±5.7 mV). Nanoparticles to which TEPITC was attached did not show a significant change in surface charge (9.4±4.2 mV). The final formulation, ROSG-pSiNP (JS-11), in which both TEPITC and CGKRK peptides (SEQ ID NO: 1) were conjugated, showed an increased particle size (303.2±84.2 nm, PDI=0.318) with a slight surface charge (0.61±3.31 mV).

In the environment of phosphate buffer saline (PBS, pH 7.4) and cell culture medium (DMEM), ROSG-pSiNP (JS-11) has a similar size distribution (PBS: 337.7±81.4 nm, DMEM: 350.8±90.9 nm), showing a negative surface charge (PBS:4.69±7.2 mV, DMEM:5.64±6.2 mV).

ROSG-pSiNP (JS-11) showed no particle aggregation or rapid decomposition in DI $H_2O$, PBS, and DMEM. This indicates the high colloidal stability of ROSG-pSiNP (JS-11).

FIG. 12 shows a transmission electron microscope (TEM) image of pSiNP and ROSG-pSiNP (JS-11). According to FIG. 12, the uniformity of the shape and size of pSiNP was maintained even after drug loading and ROS generating moiety/peptide conjugation.

According to FIG. 13, the attenuated total reflectance Fourier transform infrared (ATR-FTIR) spectrum of pSiNPs showed two bands of 3550 to 3200 $cm^{-1}$ corresponding to v(OH) stretching and 1065 $cm^{-1}$ corresponding to v(Si—O) stretching. After drug loading, the pSiNP (JS-11) formulations show the bands of 2950 to 2860 $cm^{-1}$ corresponding to v(C—H) stretching vibration of the aliphatic chain, 1710 to 1680 $cm^{-1}$ corresponding to v(C=O) stretching, and 1310 to 1250 $cm^{-1}$ corresponding to the stretching vibration for v(C–O) of the aromatic ester. This suggests that JS-11 was successfully loaded onto pSiNP ROSG-pSiNP (JS-11) nanoparticles showed characteristic bands at 2140 and 1650 $cm^{-1}$. This is due to the bending mode of isothiocyanate and the stretching vibration of the amide bond, indicating successful conjugation of the TEPITC and CGKRK peptides (SEQ ID NO: 1).

ROSG-pSiNP (JS-11) showed a loading efficiency of JS-11 at to 26.7±2.3%. The loading efficiency of JS-11 was calculated by Equation 1 below.

$$\text{loading efficiency (\%)} = \frac{W^{totalJS-11} - W^{unloaded-loadedJS-11}}{W^{loadedJS-11} + W^{NPs}} \times 100 \qquad \text{[Equation 1]}$$

The concentration of unloaded JS-11 was calculated from the standard absorption curve. To determine whether JS-11 loaded on nanoparticles was not released during the surface modification step of pSiNP (JS-11), each surface modification step [(1) calcium treatment, (2) APDMES modification, (3) NHS-PEG-MAL conjugation, (4) TEPITC modify, (5) CGKRK peptide conjugation (SEQ ID NO: 1)] were analyzed by measuring UV/vis absorption spectra.

Since the characteristic absorption peak of JS-11 was not observed in each surface modification step, it was confirmed that JS-11 loaded on pSiNP was not released during the surface modification step.

After the characterization of nanoparticles, ROSG-pSiNP were incubated with a small amount of $H_2O_2$ at 37° C. to determine whether particle degradation was induced by ROS and whether JS-11 was converted to SN-38 by ROS. pSiNP exhibit absorption at 405 nm by the Si backbone, and the transparency of pSiNP increases as it decomposes.

Figure 14A:
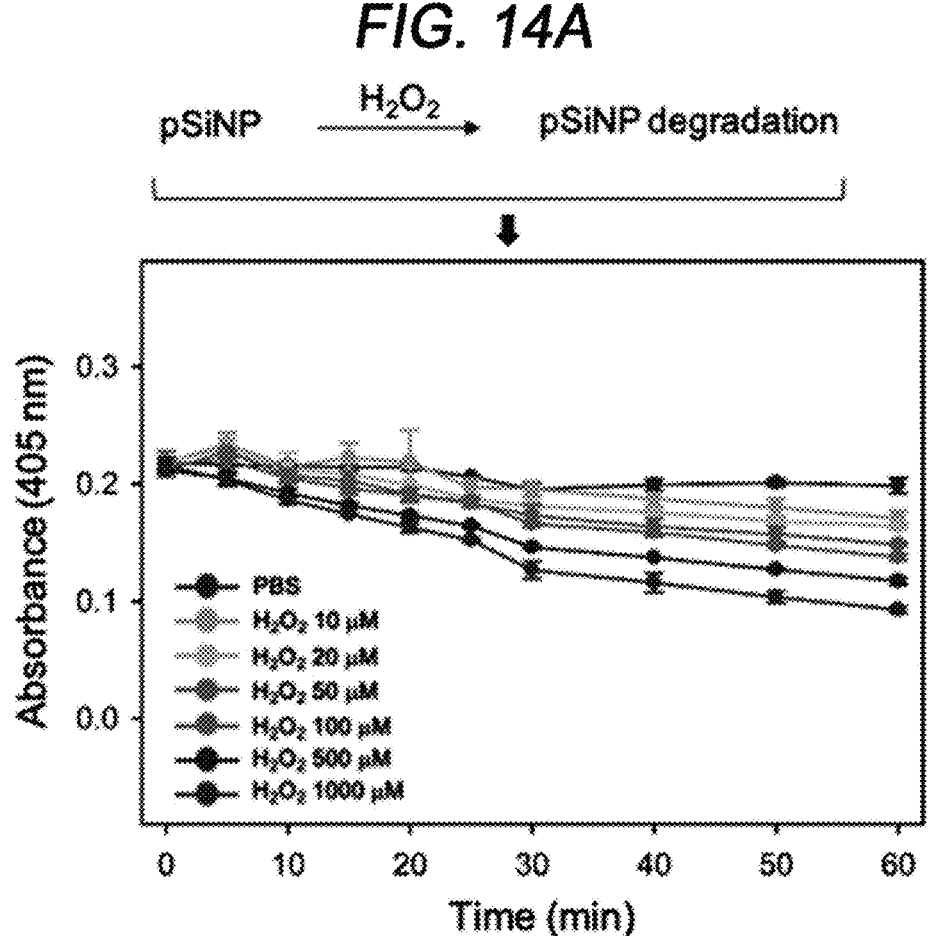
FIG. 14 shows the results of confirming the degree of decomposition of ROSG-pSiNP and the degree of conver-sion of JS-11 released from ROSG-pSiNP to SN-38 accord-ing to the concentration of hydrogen peroxide.

According to FIG. 14A, the absorption intensity of pSiNPs decreased over time (0 to 60 minutes) due to decomposition, and the decrease was increased as the concentration of $H_2O_2$ (0 to 1000 µM) increased.

The JS-11 release and SN-38 conversion profiles of ROSG-pSiNP (JS-11) were analyzed. ROSG-pSiNP (JS-11) was incubated in PBS (pH 7.4) containing $H_2O_2$ (1 mM), and the fluorescence signal of SN-38 was measured at regular time intervals (0 to 24 hours).

According to FIG. 14B, in the experimental group with $H_2O_2$, 900% or more of SN-38 was converted after 24 hours, whereas in the experimental group without $H_2O_2$, less than 20% of SN-38 was converted even after 24 hours.

Additionally, according to the TEM analysis result of FIG. 15, after 1 hour has elapsed after treatment of pSiNP with PBS or $H_2O_2$, there was no change in the shape of the nanoparticles in PBS, but decomposition proceeded in $H_2O_2$, and the shape was significantly changed. As a result, it can be seen that the degradation of pSiNP is accelerated when exposed to ROS. This is related to the formation of silanol (Si—OH) on the surface by ROS and conversion to orthosilicic acid ($Si(OH)_4$).

<Example 4> In Vitro Cytotoxicity Evaluation of ROSG-pSiNP (JS-11)

According to the in vitro analysis of the Example 3, a theoretical basis was prepared that ROSG-pSiNP (JS-11) could release the drug after self-activation by ROS within the tumor.

DCFDA/DCF analysis was performed to confirm the intracellular ROS generating ability of ROSG-pSiNP (JS-11) on BxPC-3 cells. BxPC-3 cells were treated with pSiNP, JS-11, pSiNP (JS-11), and ROSG-pSiNP (JS-11) (nanoparticle concentration of 0 to 100 µg/mL), respectively, and incubated for 5 hours.

Figure 16:
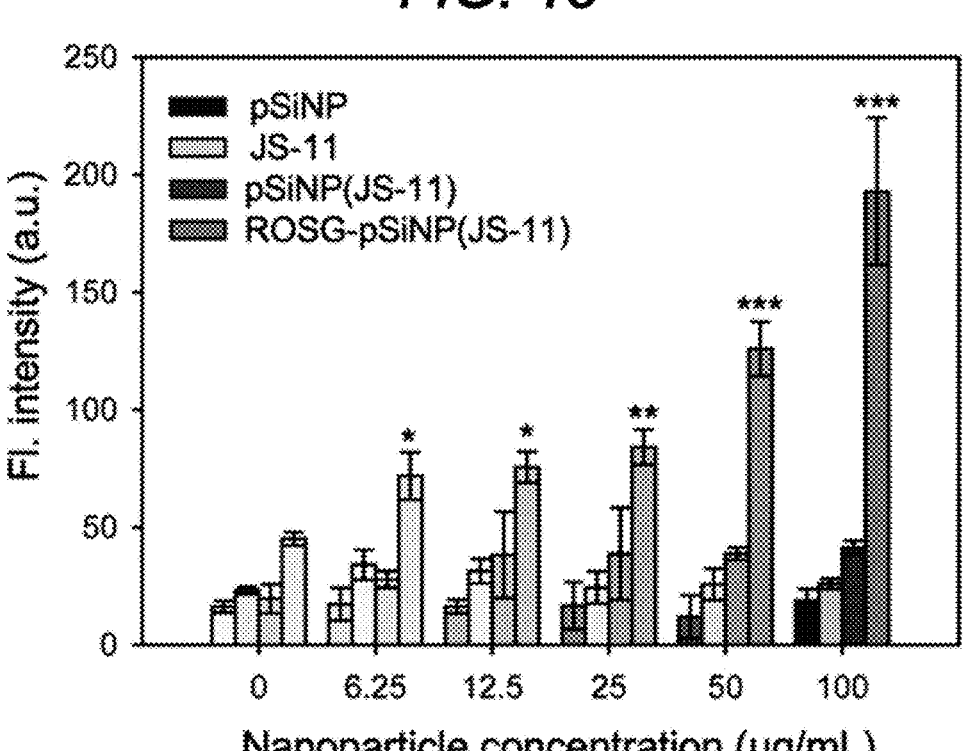
FIG. 16 shows the results of confirming the effect of ROSG-pSiNP (JS-11) on the ROS level in pancreatic cancer cells (BxPC-3) by DCF fluorescence.

According to FIG. 16, in the ROSG-pSiNPs (JS-11) treatment group, the intensity of DCF fluorescence signal increased in a dose-dependent manner. The ROS level of cells treated with 100 µg/mL of ROSG-pSiNP (JS-11) was 8.3 times higher than that of the PBS control group, and the value was consistent with the ROS level of cells treated with 325 µM $H_2O_2$. In addition, it was confirmed that the ROSG-pSiNP formulation without JS-11 had ROS generating properties.

Figure 17:
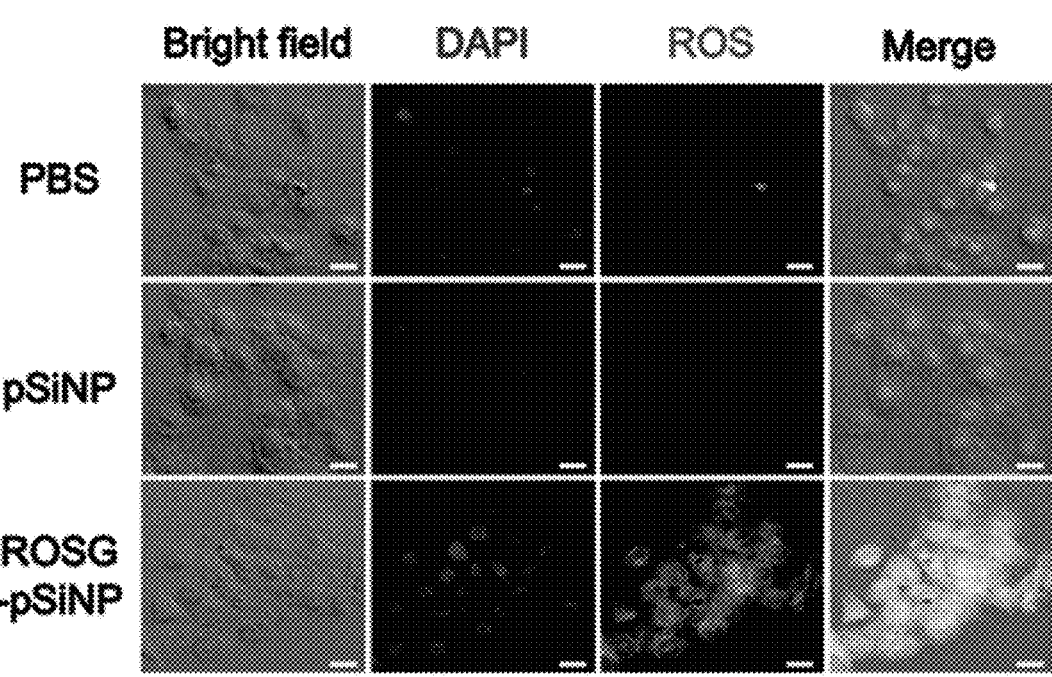
FIG. 17 shows the results of confirming the effect of ROSG-pSiNP (JS-11) on the ROS level in pancreatic cancer cells (BxPC-3) with a CLSM image.

According to the CLSM cell imaging of FIG. 17, in the experimental group treated with ROSG-pSiNP, it was observed that the fluorescence signal of DCF was higher than that of the experimental group treated with PBS and pSiNP. This was consistent with the results of cytotoxicity analysis and fluorescence signal analysis.

To confirm the hypothesis that ITC surface-modified nanoparticles increase intracellular ROS levels, BxPC-3 cells were incubated at 37° C. for 6 hours with ROSG-pSiNP (JS-11) (concentration 0 to 100 µg/mL), and GSH levels and glutathione peroxidase (GPx) enzyme activity were analyzed. In cells treated with ROSG-pSiNP (JS-11), GSH was depleted up to 75% in a dose-dependent manner, and intracellular GPx activity was also significantly reduced. These results indicate that ITC functionalized nanoparticles (ROSG-pSiNP (JS-11)) not only deplete intracellular GSH levels but also inhibit GPx activity, leading to severe ROS accumulation in BxPC-3 cells.

Figures 18, 19:
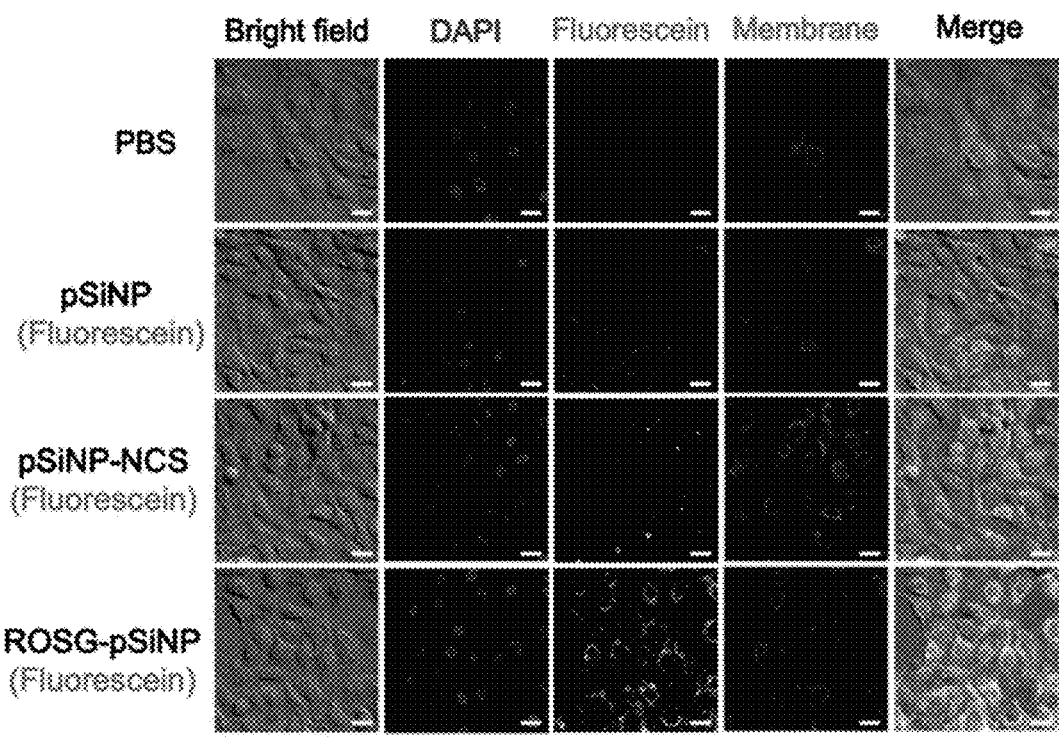
FIG. 18 shows the results of confirming the effect of ROSG-pSiNP (JS-11) on Nrf2 expression in BxPC-3 cells by Western blot.
FIG. 19 shows the results of confirming the degree of uptake of pSiNP, pSiNP-NCS, and ROSG-pSiNP (JS-11) in BxPC-3 cells with a CLSM image.

According to FIG. 18, in the ROSG-pSiNP treated group, Nrf2 expression appeared 2 hours after the start of incubation, and the results were consistent with the DCF analysis results. Analysis of CLSM imaging and Nrf2 expression levels using pSiNP without JS-11 loading confirmed that intracellular oxidative stress and ROS generation were not induced by JS-11.

The cancer-targeting ability of ROSG-pSiNP (JS-11) was further investigated. BxPC-3 cells were incubated with (i) fluorescein loaded pSiNP, (ii) fluorescein loaded TEPITC functionalized pSiNP, and (iii) fluorescein loaded TEPITC/ CGKRK (SEQ ID NO: 1) functionalized pSiNP at 37° C. for 24 hours. DAPI staining and cell mask plasma membrane staining were performed, and the fluorescence signal of fluorescein was analyzed using confocal laser scanning microscopy (CLSM) imaging, and the cellular uptake and intracellular localization of nanoparticles were confirmed.

According to FIG. 19, targeted nanoparticles, ROSG-pSiNP (fluorescein loaded pSiNP with TEPITC/CGKRK (SEQ ID NO: 1) functionalization), were found to have higher absorption in BxPC-3 cells than non-targeted nanoparticles (fluorescein loaded pSiNP and fluorescein loaded TEPITC functionalized pSiNP). In images containing DAPI and cell mask plasma membrane dye, the fluorescein signal (green) was mainly observed in the cytoplasm, which means that particles penetrated the cell efficiently.

Next, the cytotoxicity of pSiNP, JS-11, pSiNPs (JS-11), and ROSG-pSiNP (JS-11) was evaluated for BxPC-3 cell lines. The throughput of pSiNP (JS-11) and ROSG-pSiNP (JS-11) was corrected with the concentration of JS-11 (0 to 10 μM).

Figure 20:
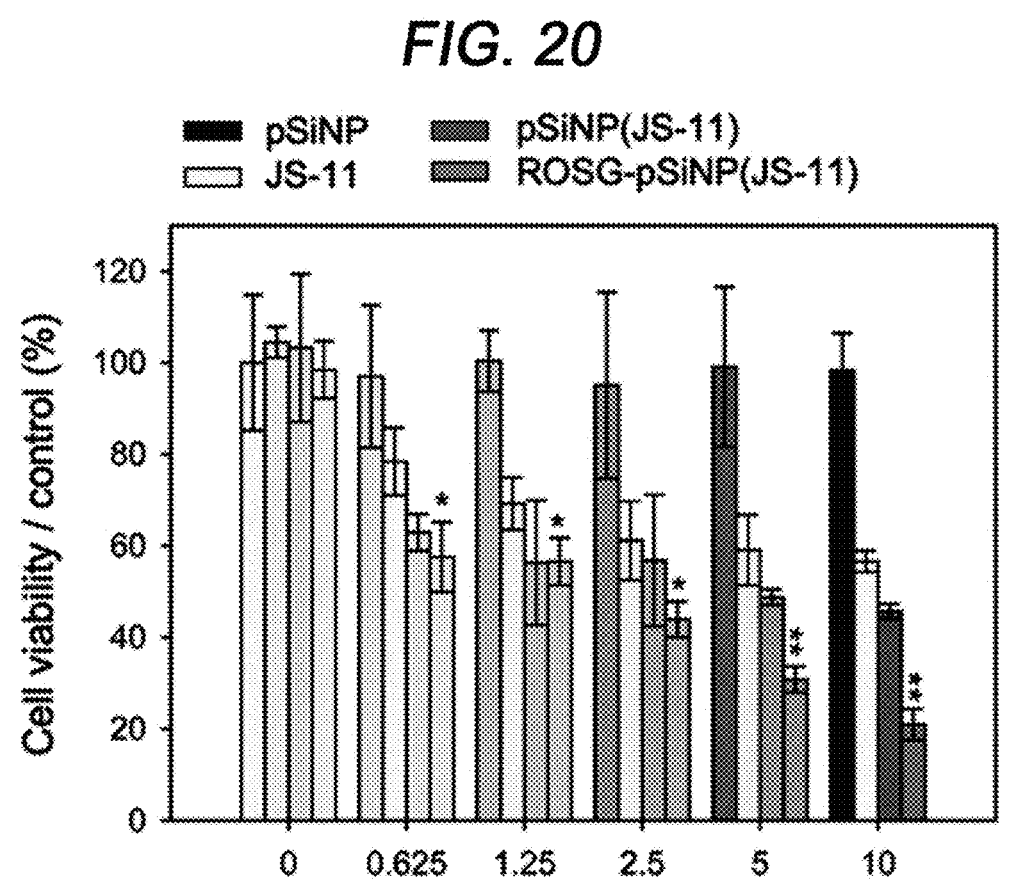

According to FIG. 20, the negative control pSiNP had very low cytotoxicity, but the rest showed significant toxicity in a dose-dependent manner. The group treated with ROSG-pSiNP (JS-11) showed the highest toxicity. The results were as follows: (i) at low concentration (0.625 μM JS-11): JS-11 was 21.60%; pSiNP (JS-11) was 31.11%; and ROSG-pSiNP (JS-11) is 42.5%, (ii) at high concentration (10 μM JS-11): JS-11 was 42.4%; pSiNP (JS-11) was 54.3%; and ROSG-pSiNP (JS-11) was 79.1%.

The cytotoxicity of two nano-formulations, pSiNP-NCS (without JS-11 and TEPITC-modifying) and pSiNP-NCS/ CGKRK (SEQ ID NO: 1) (without JS-11 and CGKRK-modifying), was further analyzed to confirm the synergistic cytotoxic effect of JS-11 and TEPITC. At low concentration (0.625 μM JS-11, 12.5 μg/mL nanoparticles), pSiNP-NCS and pSiNP-NCS/CGKRK (SEQ ID NO: 1) showed lower toxicity than nanoparticles containing JS-11 nano-formulation. pSiNP-NCS was 16.7% and pSiNP-NCS/CGKRK (SEQ ID NO: 1) was 33.1%, while pSiNP (JS-11) was 31.11% and ROSG-pSiNP (JS-11) was 42.5%. At high concentration (10 μM JS-11, 100 g/mL nanoparticles), pSiNP-NCS (53.1%) and pSiNP-NCS/CGKRK (SEQ ID NO: 1) (67.1%) showed lower toxicity than that of ROSG-pSiNP (JS-11) (79.1%).

The higher toxicity of pSiNPs (JS-11) than JS-11 was due to the improved cell penetration, and the higher toxicity of ROSG-pSiNPs (JS-11) is due to their higher toxicity than pSiNPs (JS-11) and nanoparticles without JS-11 (pSiNP-NCS and pSiNP NCS/CGKRK). This is thought to cause a synergistic effect by the combination of cell penetration improvement by CGKRK peptide (SEQ ID NO: 1), in situ ROS generation by TEPITC moiety, and conversion from JS-11 to SN-38 in cells.

<Example 5> In Vivo Anti-Cancer Effect of ROSG-pSiNP (JS-11)

The cancer-specific therapeutic efficacy of ROSG-pSiNP (JS-11) has been demonstrated in the xenograft mice model for pancreatic cancer.

First, the hemolytic properties of ROSG-pSiNP (JS-11) were investigated to confirm safety during intravenous injection. Red blood cells were incubated at 37° C. for 1 hour in a solution containing 0.1 mg/nL of ROSG-pSiNP (JS-11). PBS and Triton X-100 were used as negative and positive control groups, respectively. ROSG-pSiNP (JS-11) showed a negligible hemolysis rate of <1% in red blood cells (p<0.001), thus confirming excellent safety for intravenous injection.

Figure 21:
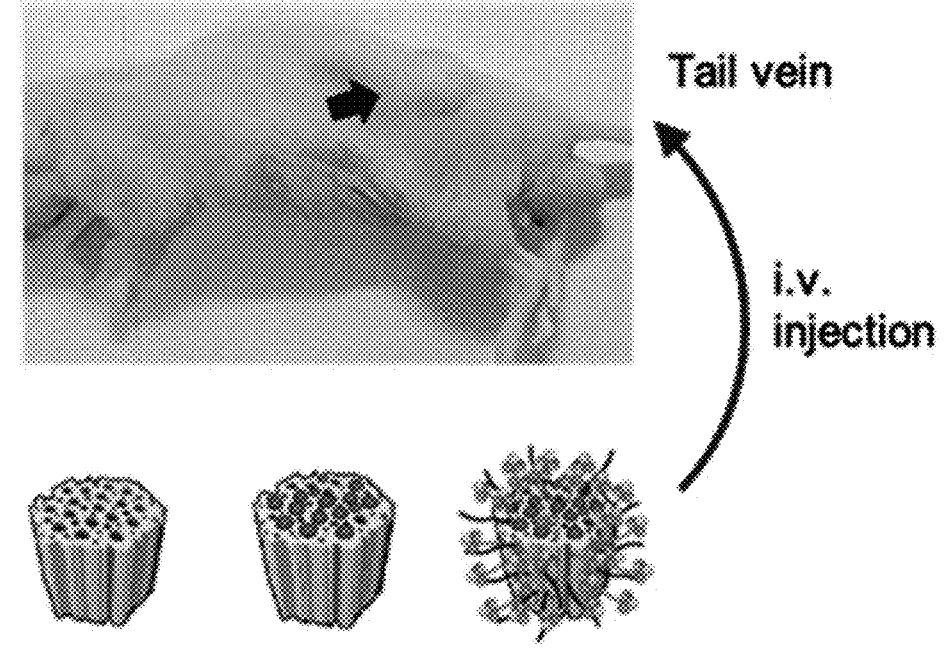
FIG. 21 shows the experimental process of administering pSiNP, pSiNP (JS-11), and ROSG-pSiNP (JS-11) to pancre-atic cancer xenograft mice.

Next, the biodistribution of ROSG-pSiNP (JS-11), pSiNP (empty), and JS-11-loaded pSiNP was confirmed. The nanoparticles were administered intravenously (i.v.) at a dose of 20 mg/kg to pancreatic cancer model mice. (See FIG. 21). 1 hour and 2 hours after nanoparticle injection, internal organs (heart, lung, liver, kidney, and spleen) and tumors were obtained and analyzed for pSiNP intrinsic photoluminescence (PL).

For organs and tumors 1 hour after injection, the control group (PBS injected) did not show tissue autofluorescence signals, but all nano-formulations (pSiNP, pSiNP (JS-11), and ROSG-pSiNP (JS-11)) showed a strong signals in at the heart, lung, liver and kidney compared to the tumor site.

Figure 22:
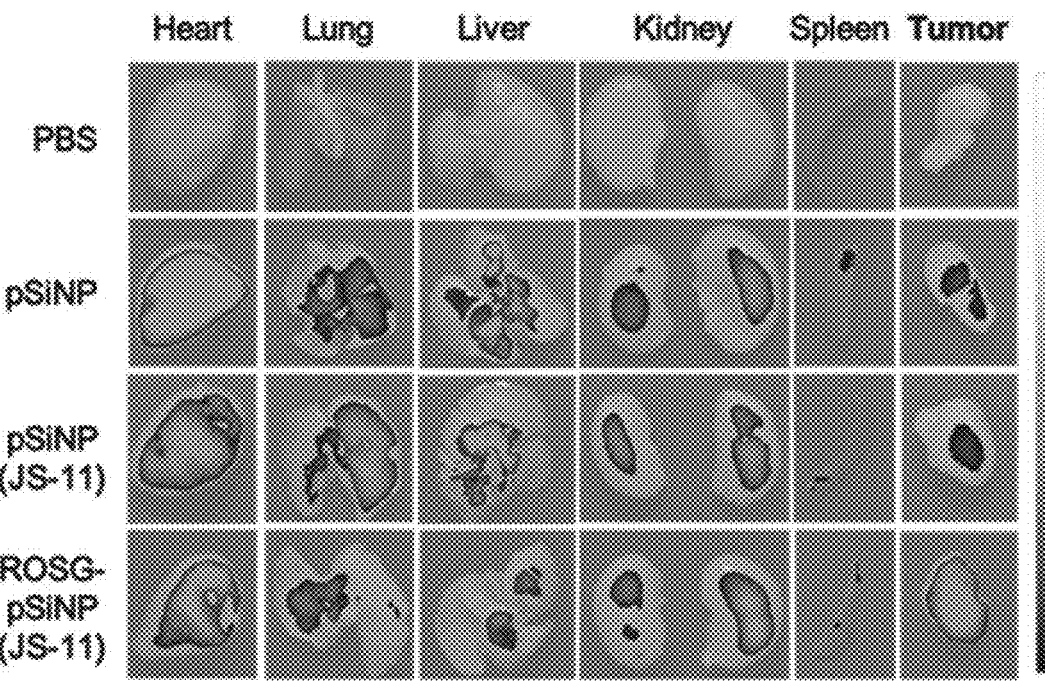
FIG. 22 shows the results of intravenous injection of pSiNP, pSiNP (JS-11), and ROSG-pSiNP (JS-11) into pan-creatic cancer xenograft mice and confirms the degree of organ and tumor distribution after 2 hours.
Figure 23:
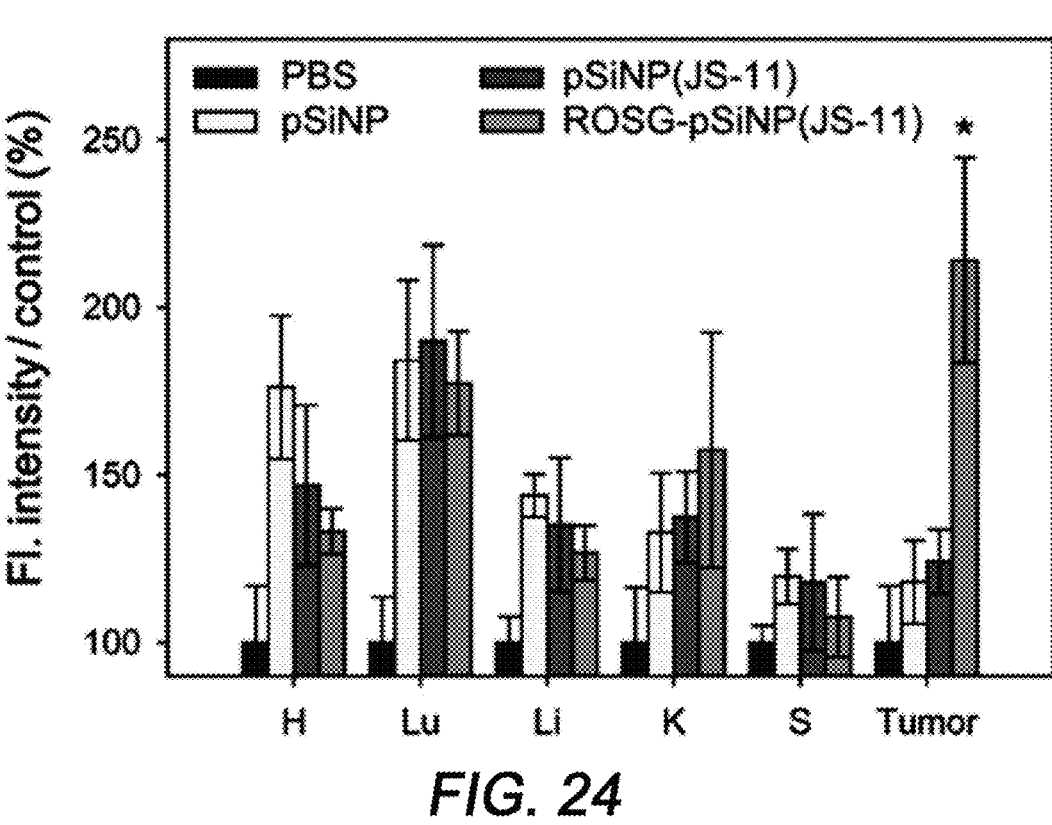
FIG. 23 shows the PL signals of organs and tumor distribution after intravenous injection of pSiNP, pSiNP (JS-11), and ROSG-pSiNP (JS-11) into pancreatic cancer xenograft mice.

However, 2 hours after injection, accumulation in the liver and kidneys decreased dramatically. In addition, according to FIGS. 22 and 23, the non-targeted nano-formulations (pSiNP and pSiNP (JS-11)) showed stronger PL signals in the heart, lung, kidney, and liver than in tumor, but the targeted nano-formulation ROSG-pSiNP (JS-11) showed a decreased signal in organs and a stronger signal within the tumor site.

The process of ROSG-pSiNP (JS-11) removal in vivo was analyzed. ROSG-pSiNP (JS-11) was intravenously injected into BALB/c mice at a dose of 20 mg/kg, and the mice were sacrificed after 2 hours and 24 hours circulation. Major organs (lung, heart, liver, spleen, and kidney) were obtained and the PL signal of pSiNP was measured. At the 2-hour cycle time point, ROSG-pSiNP (JS-11) was mainly accumulated in the liver and kidney. However, at the time of 24-hour circulation, ROSG-pSiNP (JS-11) accumulated in the organ was significantly removed. Since the removal mechanism of pSiNP is known to be excreted after decomposition into soluble silicic acid $(Si(OH)_4)$, it is thought that ROSG-pSiNP (JS-11) will also be removed from the body by the same mechanism.

Finally, the cancer treatment efficacy of ROSG-pSiNP (JS-11) was evaluated in pancreatic cancer xenograft model mice. To induce pancreatic tumors, BxPC-3 cells were injected subcutaneously behind the flank of mice on day 0. The tumor size after 4 weeks of injection of BxPC-3 cells was about 150 mm³. On days 34, 37, 40, and 43 after tumor injection, PBS, JS-11, pSiNP (JS-11), and ROSG-pSiNP (JS-11) were administered to mice with pancreatic tumors at doses of 20 mg/kg via tail veins. Changes in tumor volume and body weight in mice were monitored, and toxic effects were investigated for practical applications.

Figure 24:
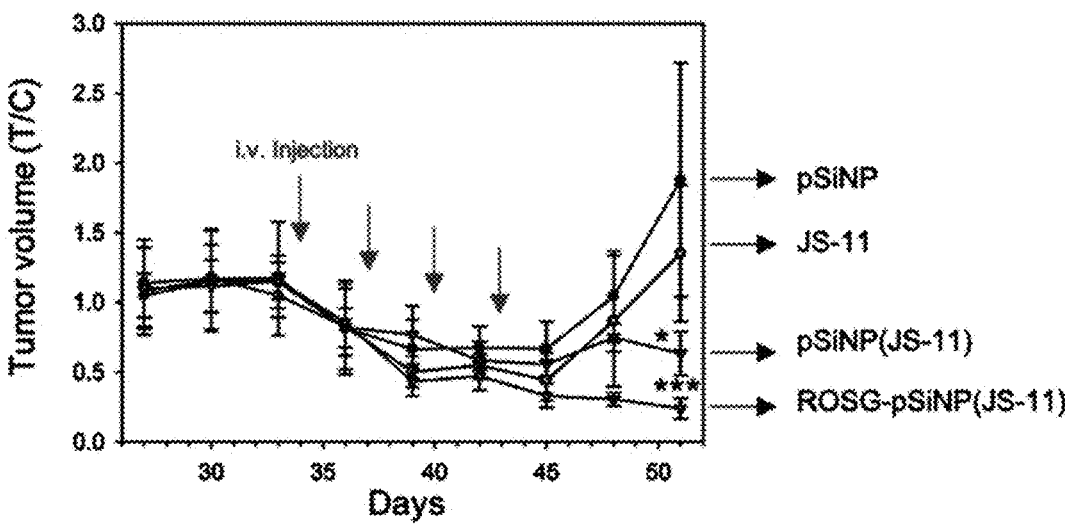
FIGS. 24 and 25 are results of confirming the change in tumor size after administration of pSiNP, JS-11, pSiNP (JS-11), or ROSG-pSiNP (JS-11) to pancreatic cancer xeno-graft mice.

According to FIG. 24, the experimental group administered with ROSG-pSiNP (JS-11) showed a significant decrease in tumor volume as of day 51 compared to the experimental group administered with empty pSiNP, JS-11, and pSiNP (JS-11).

Figure 25A:
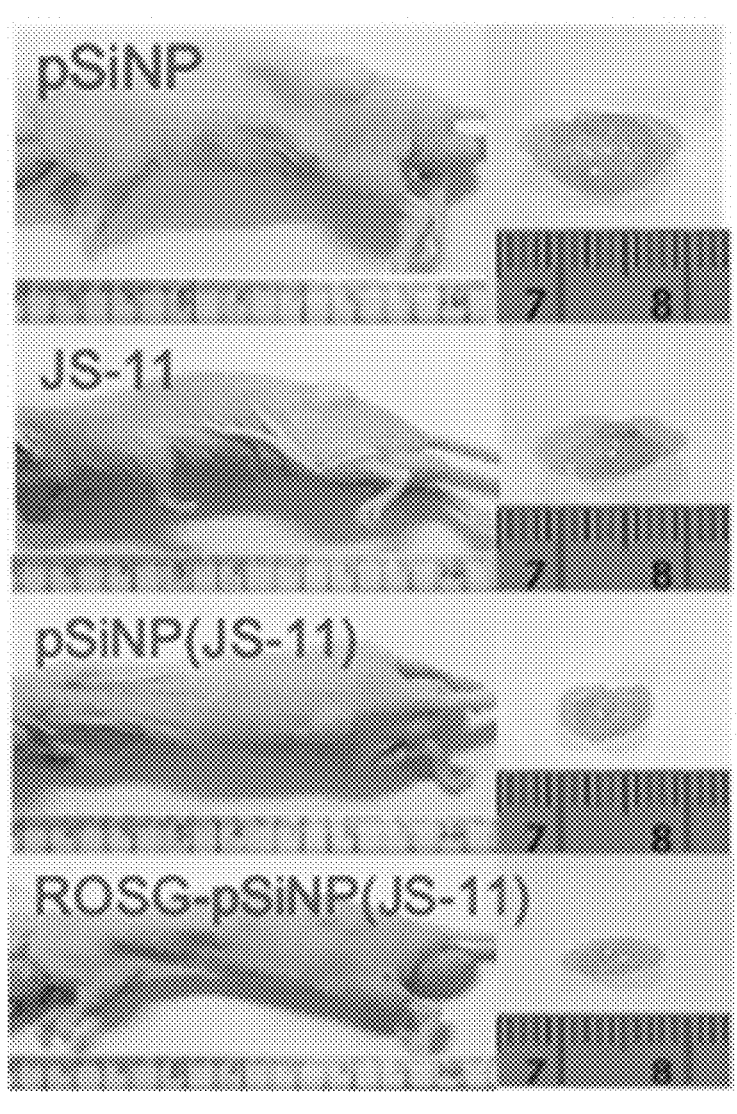

According to FIG. 25, pSiNP and pSiNP (JS-11) slightly reduced tumor size, whereas ROSG-pSiNP (JS-11) dramatically reduced tumor size. The mean tumor volume of the ROSG-pSiNP (JS-11) treated group was $93.5 \pm 22.7$ mm$^3$, whereas the mean tumor volume of the pSiNP, JS-11, and pSiNP (JS-11) treated groups was $259.6 \pm 57.8$ mm$^3$, $183.1 \pm 40.8$ mm$^3$, and $179.0 \pm 37.6$ mm$^3$, respectively. No significant body weight change occurred in all mice injected with nanoparticles.

The hepatotoxicity of pSiNP, JS-11, pSiNP (JS-11), and ROSG-pSiNP (JS-11) was analyzed by measuring plasma levels of alanine transferase (ALT) and aspartate transami- Nrf2/HO-1 protein expression related to oxidative stress in tumor tissues was observed by immunohistochemistry experiments.

Figure 27:
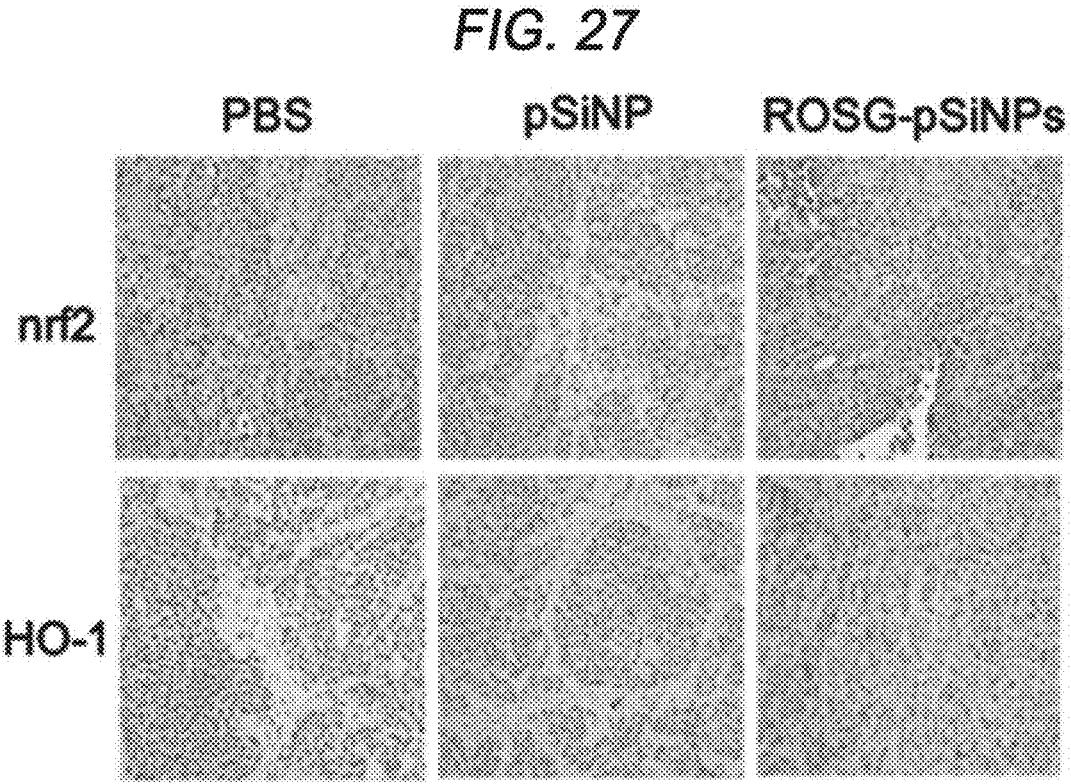
FIG. 27 is a result of administering pSiNP, JS-11, pSiNP (JS-11), or ROSG-pSiNP (JS-11) to pancreatic cancer xeno-graft mice and observing the expression of Nrf2/HO-1 protein in tumor tissue through an immunohistochemistry experiment.

According to FIG. 27, it was confirmed that the expression of Nrf2 and HO-1 proteins increased in the tumor tissue administered with the ROSG-pSiNP formulation, which was consistent with the in vitro results. Summarizing the experimental results, the ROSG-pSiNP (JS-11) formulation can selectively and significantly reduce the size of pancreatic cancer without weight loss and hepatotoxicity by inducing tumor-specific ROS generation and oxidative stress.

SEQUENCE LISTING

```
<160> NUMBER OF SEQ ID NOS: 3

<210> SEQ ID NO 1
<211> LENGTH: 5
<212> TYPE: PRT
<213> ORGANISM: Artificial Sequence
<220> FEATURE:
<223> OTHER INFORMATION: tumor homing peptide

<400> SEQUENCE: 1

Cys Gly Lys Arg Lys
1               5

<210> SEQ ID NO 2
<211> LENGTH: 5
<212> TYPE: PRT
<213> ORGANISM: Artificial Sequence
<220> FEATURE:
<223> OTHER INFORMATION: tumor homing peptide

<400> SEQUENCE: 2

Cys Arg Glu Lys Ala
1               5

<210> SEQ ID NO 3
<211> LENGTH: 3
<212> TYPE: PRT
<213> ORGANISM: Artificial Sequence
<220> FEATURE:
<223> OTHER INFORMATION: tumor homing peptide

<400> SEQUENCE: 3

Arg Gly Arg
1
``` nase (AST), which are hepatotoxicity markers. 20 mg/kg of nanoparticles (pSiNP, pSiNP (JS-11), and ROSG-pSiNP (JS-11)) and corresponding concentration of JS-11 (5.2 mg/kg) were injected into the tail vein of pancreatic cancer xenograft model mice. On day 51, after BxPC-3 cell inoculation, plasma AST/ALT levels were analyzed.

Figures 25B, 26:
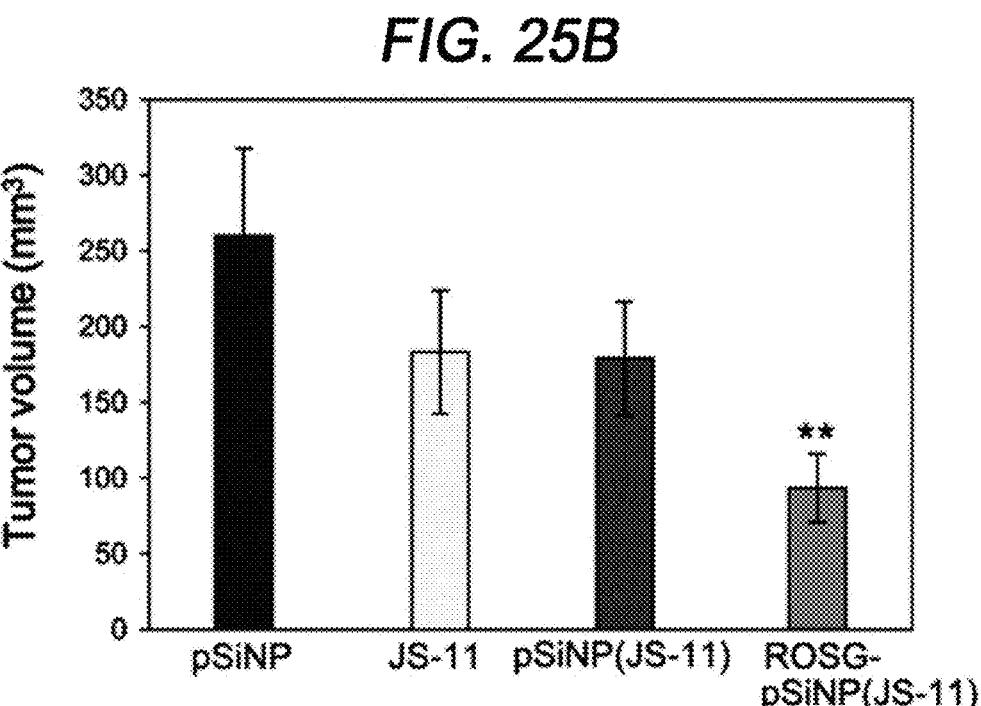
FIG. 26 is a result of confirming plasma AST/ALT levels and hepatotoxicity after administration of pSiNP, JS-11, pSiNP (JS-11), or ROSG-pSiNP (JS-11) to pancreatic cancer xenograft mice.

According to FIG. 26, hepatotoxicity was not shown in the PBS, pSiNP, pSiNP (JS-11), and ROSG-pSiNP (JS-11) treatment groups (AST<200 U/L, ALT<60 U/L), but the JS-11 treatment groups had 2.8 and 3.5 times higher AST levels than the PBS control groups, respectively. According to the experimental results, since pSiNP (JS-11) and ROSG-pSiNP (JS-11) do not release drugs during liver metabolism, it suggests that tumor-specific delivery of JS-11, a highly hepatotoxic anticancer drug, can lower side effects and increase therapeutic effects.

What is claimed is:

1. A pharmaceutical composition for treating pancreatic cancer comprising a drug delivery system comprising:
   a porous silicon nanoparticle;
   an isothiocyanate moiety conjugated to the surface of the porous silicon nanoparticle,
   wherein the drug delivery system further comprises a prodrug supported on the porous silicon nanoparticle, and
   a tumor homing peptide conjugated to the surface of the porous silicon nanoparticle,
   wherein the tumor homing peptide consists of a peptide having an amino acid sequence consisting of CGKRK (SEQ ID NO.1,
   wherein the prodrug is converted into an active drug by removing a promoiety ester-bonded with a parent drug by reactive oxygen species, wherein the parent drug is 7-ethyl-10-hydroxycamptoth-
ecin, wherein the promoiety is mefenamic acid wherein the parent drug is a camptothecin-based antican-
cer agent, and wherein the drug delivery system is represented by the
following Formula 2,

[Formula 2]

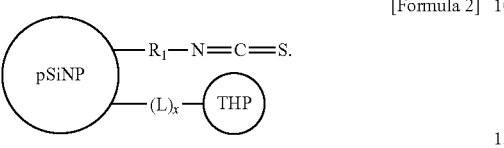

in Formula 2, pSiNP is the porous silicon nanoparticle, the R 1 —N═C═S is the isothiocyanate moiety, the isothiocyanate moiety is derived from triethoxy(3-
isothiocyanatopropyl)silane), the R 1 is propyl, the THP is the tumor homing peptide, the L is a PEG linker, and X is 1.

2. A method for manufacturing the drug delivery system
of claim 1, the method comprising:

preparing a porous silicon nanoparticle, and conjugating
an isothiocyanate moiety to the surface of the porous
silicon nanoparticle;

supporting a prodrug on the porous silicon nanoparticle;
and conjugating a tumor homing peptide to the surface of the
porous silicon nanoparticle.

* * * * *